US008006576B2

(12) United States Patent
Decker

(10) Patent No.: US 8,006,576 B2
(45) Date of Patent: Aug. 30, 2011

(54) CONDENSATION COLLECTION DEVICE AND METHODS OF USE

(75) Inventor: David Louis Decker, Reno, NV (US)

(73) Assignee: Board of Regents of the Nevada System of Higher Education, on Behalf of the Desert Research Institute, Reno, NV (US)

( * ) Notice: Subject to any disclaimer, the term of this patent is extended or adjusted under 35 U.S.C. 154(b) by 769 days.

(21) Appl. No.: 12/103,642

(22) Filed: Apr. 15, 2008

(65) Prior Publication Data

US 2009/0255350 A1 Oct. 15, 2009

(51) Int. Cl.
*G01N 1/22* (2006.01)
(52) U.S. Cl. .................................. 73/863.11
(58) Field of Classification Search .............. None
See application file for complete search history.

(56) References Cited

U.S. PATENT DOCUMENTS

| | | | |
|---|---|---|---|
| 4,464,338 A | 8/1984 | Dotson et al. | |
| 4,551,298 A | 11/1985 | Goldstein et al. | |
| 4,755,471 A | 7/1988 | Saito et al. | |
| 4,835,395 A | 5/1989 | McManus et al. | |
| 5,080,693 A | 1/1992 | Bourne et al. | |
| 5,211,679 A * | 5/1993 | Meyer | 73/863.12 |
| 5,264,702 A | 11/1993 | Mihalczo | |
| 5,319,955 A | 6/1994 | Chastagneri | |
| 5,326,482 A * | 7/1994 | Lessard et al. | 210/743 |
| 5,783,828 A | 7/1998 | Pacenti et al. | |
| 5,794,695 A | 8/1998 | Peterson | |
| 6,110,397 A | 8/2000 | Shepodd et al. | |
| 6,159,427 A | 12/2000 | Kherani | |
| 6,295,864 B1 * | 10/2001 | You et al. | 73/53.01 |
| 2002/0112992 A1 * | 8/2002 | Johnson et al. | 208/305 |
| 2004/0184987 A1 | 9/2004 | Ring et al. | |
| 2007/0017291 A1 * | 1/2007 | Cypes et al. | 73/590 |
| 2007/0147467 A1 * | 6/2007 | Arnold et al. | 374/28 |
| 2008/0045825 A1 * | 2/2008 | Melker et al. | 600/365 |

(Continued)

FOREIGN PATENT DOCUMENTS

WO WO2008/021601 A2 2/2008

OTHER PUBLICATIONS

Brown, R.M., et al., "The Determination of Tritium in Natural Waters," *Canadian Journal of Chemistry*, 34 (1956).

(Continued)

*Primary Examiner* — Robert Raevis
(74) *Attorney, Agent, or Firm* — Ryan A. Heck; UNR-DRI Technology Transfer Office

(57) ABSTRACT

In certain aspects, the present disclosure provides a monitoring device that includes a condensation unit and a detector, such as a proportional detector. The condensation unit includes a condensation surface, a cooler abutting the condensation surface, and a collection vessel in fluid communication with the condensation surface. The monitoring device may include a decomposition reactor, such as an electrolytic reactor or a reactor that includes an active metal, such as an alloy of sodium and potassium. Particular implementations include a housing that at least partially encloses the condensation unit. The housing may include an aperture, which may be covered by a screen, mesh, or filter. The housing may also include a fan. The fan is used, in some examples, to draw air through the aperture. The monitoring device is, in some implementations, configured for remote operation, such as including a power supply or transmitter.

22 Claims, 19 Drawing Sheets

U.S. PATENT DOCUMENTS

2009/0114828 A1    5/2009    Decker et al.

OTHER PUBLICATIONS

Chaudron, V., et al., "Experimental Evaluation of Hydrogen Getters as Mitigation Technique in a Fusion Reactor," IEEE p. 208-211 (1998).

Decker, D.L., et al., "Subsurface In Situ Tritium Monitoring Instrument Development: Interim Report." DHS Publication No. 41227, (Jul. 2006).

"Down-Hole Tritium in Water Detector," Technical Associates Product Literature, 7051 Eton Ave., Canoga Park, CA 91303 (Jan. 2002).

Esarte, J., "Incipient Cavitation in a Steering Rotary Valve," *Fluent News*, Fall 2005, http://www.fluent.com/about/news/newsletters/05v14i3/a12.htm, (web link accessed May 8, 2006).

Fukui, et al., "Oxidized Tritium Around a Research Reactor Site," *J. Nuclear Sci. & Tech.*, 42(9):816-824 (Sep. 2005).

Haas, W.J., et al., "Sensors and Monitoring Systems for Long-Term Performance Monitoring—Three Perspectives," *Long-Term Performance Monitoring of Metals and Radionuclides in the Subsurface: Strategies, Tools and Case Studies-Workshop*, Apr. 21-22, Reston, VA, available at http://cistems.fsu.edu/PDF/haas.pdf (available at least as early as May 18, 2007).

International Atomic Energy Agency, "Safe Handling of Tritium," Vienna, 39 pp. (1991).

Jones, J.B., et al., "The Advanced Monitoring System Initiative: Optimizing Delivery and Application of New Sensor and Monitoring Solutions." *Accelerating Site Closeout, Improving Performance, and Reducing Costs Through Optimization*, Jul. 15-17, 2004, Dallas, TX, available at www.clu-in.org/siteopt/proceedings_04/track_b/wed/12_jones_john.pdf (Jul. 2004).

Karmen, et al., "Measurement of Tritium in the Effluent of a Gas Chromatograph." *Anal. Chem.* 35(4):536-542 (1963).

Kaufman, S., et al., "The Natural Distribution of Tritium," *Physical Review*, 93(6) (1954).

Kherani, N.P., "An Alternative Approach to Tritium-in-Water Monitoring," *Nuclear Instruments and Methods in Physics Research A*, 484:650-659 (2002).

Kim, S.H., International Search Report and Written Opinion of the International Searching Authority (Mar. 11, 2008).

Knoll, G.F., *Radiation Detection and Measurement*, $3^{rd}$ Ed., John Wiley and Sons, Inc. ISBN 0-471-07338-5 (2000).

Neary, M.P., "Tritium Enrichment—To Enrich or Not to Enrich," *Radioactivity & Radiochemistry*, 8(4):23-35 (1997).

Technology Management System, "Down-Hole Tritium Analysis System for Deep Monitoring Wells," http://mfnl.xjtu.edu.cn/gov-doe-netl/products/em/IndUnivProg/pdf/3171.pdf (document dated Sep. 2002, web link accessed at least as early as May 15, 2006).

Tsoulfanidis, N., "Measurement and Detection of Radiation," $2^{nd}$ Ed., Taylor and Francis, Washington DC, 614 pp. (1995).

Uda, T., et al., "Developments of Gaseous Water, Hydrogen and Methane Sampling System for Environmental Tritium Monitoring," *Fusion, Engineering and Design*, 81:1385-1390 (Jan. 2006).

U.S. Department of Energy, Washington, DC, *Primer on Tritium Safe Handling Practices*, 1994. DOE-HDBK-1079-94. http://www.eh.doe.gov/techstds/standard/hdbk1079/hdb1079.html.

Venedam, R.J., Hohman, E.O., Lohrstorfer, C.F., Weeks, S.J., "Advanced Monitoring System Initiative." WM'04 Conference, Feb. 29-Mar. 4, 2004, Tucson, AZ (2004).

\* cited by examiner

CONDENSATION COLLECTION DEVICE AND METHODS OF USE

FIELD

The present disclosure relates to apparatus and methods for obtaining liquid samples by condensing vapor and detecting substances of interest in the samples. In particular embodiments, subsurface borehole tritium monitoring devices are provided.

BACKGROUND

Nuclear tests, such as those conducted at the Nevada Test Site (NTS), are often conducted below ground, such as at or below the groundwater table. These tests inject various radionuclides, including tritium, into the groundwater. Groundwater wells have been drilled at and near the NTS to sample the groundwater for radionuclides. The wide range of half-lives of the radionuclides of concern means that subsurface monitoring for some of these constituents will occur for the foreseeable future. Some of these radionuclides and their associated half-lives are: $^3$H (12.3 yrs), $^{90}$Sr (28.8 yrs), $^{137}$Cs (30.1 yrs), and $^{238}$U (4.47E+9 yrs).

While tritium has a relatively short half-life, tritium is of interest because of its groundwater transport characteristics. Tritium generally does not react with rock and mineral surfaces of an aquifer during groundwater transport. As a consequence, tritium typically moves at the average groundwater velocity and usually is transported ahead of other reactive radionuclides. Accordingly, tritium arrival in a monitoring well can be an indicator of subsequent arrival of other radionuclides.

Current sampling procedures for tritium typically include installing a pump in a monitoring well and removing at least three well volumes of fluid. Such procedures typically require specific fluid management protocols, collecting a sample, removing the pump and pump string, and decontaminating these components. The U.S. Department of Energy (DOE) has estimated that sampling 200 monitor wells for 100 years using current practices would cost over $150 million in 2005 dollars.

Tritium emits a low-energy β-particle (18.6 KeV). Current typical tritium analysis systems are based on liquid scintillation, where a water sample is collected and mixed with a "cocktail" of organic compounds that emit light when struck by the tritium β-particle. A photomultiplier tube amplifies the signal sufficiently to provide an accurate electronic representation of the tritium activity.

Dissolved radioactive ions such as $^{14}$C (156.5 KeV), $^{40}$K (1,460 KeV), $^{226}$Rn (6,000 KeV), and $^{238}$U (4,196 KeV) are nearly always present in groundwater. The presence of these ions raises the background radiation level and can reduce the ability to detect tritium against background radiation. Consequently, water must typically be purified to reduce the concentration of these ions to a sufficiently low level.

Although tritium in liquid samples is often of interest, tritium present in vapor form, such as in an underground vapor plume or in the air surrounding a surface site, such as a facility suspected of nuclear activity, may also be of interest. Typical monitoring techniques draw large samples of air to a land-surface mounted cold finger or cold point condenser system to collect vapor, such as soil vapor. These systems can suffer from a number of drawbacks, however. For example, because of the large volume of air actively pumped to the detector, such as from an unsaturated zone, the air can be representative of a large subsurface soil volume. Accordingly, the positional accuracy or precision of such monitoring systems can be greatly diminished. Furthermore, these systems are often expensive, large, and require many kilowatts of power to operate—limiting their use for remote, discrete, or long term radiological monitoring of sites.

SUMMARY

In certain aspects, the present disclosure provides a monitoring device including a detector and a condensation unit. The condensation unit includes a condensation surface, a cooler, such as a Peltier cooler, abutting the condensation surface, and a collection vessel in fluid communication with the condensation surface to receive condensed fluid. In particular implementations, the detector is a proportional detector. In further implementations, the device includes a getter unit or a pump in communication with the detector. In some embodiments, the collection vessel is omitted or the condensation surface is integrated into the cooler.

Particular embodiments of the monitoring device are configured for remote operation. Certain implementations include a transmitter that transmits data to a remote system. Further disclosed embodiments include a power supply, such as a battery or a solar cell.

In further embodiments, the monitoring device includes a decomposition reactor or a gasification reactor. The reactor converts a sample, typically an aqueous sample, into a gas, typically including a hydrogen gas, including isotopes thereof. In one specific configuration, the reactor includes an active metal, such as an alloy of sodium and potassium. In a further specific configuration, the reactor is an electrolytic reactor.

In some aspects, the monitoring device includes a housing at least partially enclosing the condensation unit. In particular implementations, the housing includes an aperture, which may be covered by a filter, mesh, or screen. Further implementations include a fan in communication with a fan aperture in the housing. The fan is used, in some examples, to draw air through the housing or cool the condensation unit. The condensation unit can include other heat sinks, such as a thermally conductive material contacting a hot surface of the cooler and a cooling source, such as colder ambient air.

The present disclosure also provides sample collection methods. In certain embodiments, the method includes obtaining a vapor sample, such as a vapor sample from a well or an ambient vapor sample from a test site. The sample is passed over a cooler, such as a Peltier cooler having a condensation surface. A component of the vapor sample, such as water, condenses on the condensation surface. The condensate is collected in a collection vessel and transferred to a detector, such as a proportional detector. A component of interest of the condensate, such as tritium, is detected. In some implementations, the condensate is transferred directly from the condensation surface to the detector.

In particular implementations, the method includes decomposing at least a portion of the condensate. For example, water may be decomposed into hydrogen gas, including isotopes thereof. For instance, water may be reacted with an active metal, such as an alloy of potassium and sodium. In a further example, water is electrolytically decomposed into hydrogen gas, including isotopes thereof.

There are additional features and advantages of the various embodiments of the present disclosure. They will become evident as this specification proceeds.

In this regard, it is to be understood that this is a brief summary of the various embodiments described herein. Any given embodiment of the present disclosure need not provide all features noted above, nor must it solve all problems or address all issues in the prior art noted above.

DETAILED DESCRIPTION

Unless otherwise explained, all technical and scientific terms used herein have the same meaning as commonly understood by one of ordinary skill in the art to which this disclosure belongs. In case of any such conflict, or a conflict between the present disclosure and any document referred to herein, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, as well as A and B together. All numerical ranges given herein include all values, including end values (unless specifically excluded) and intermediate ranges.

Figure 1:
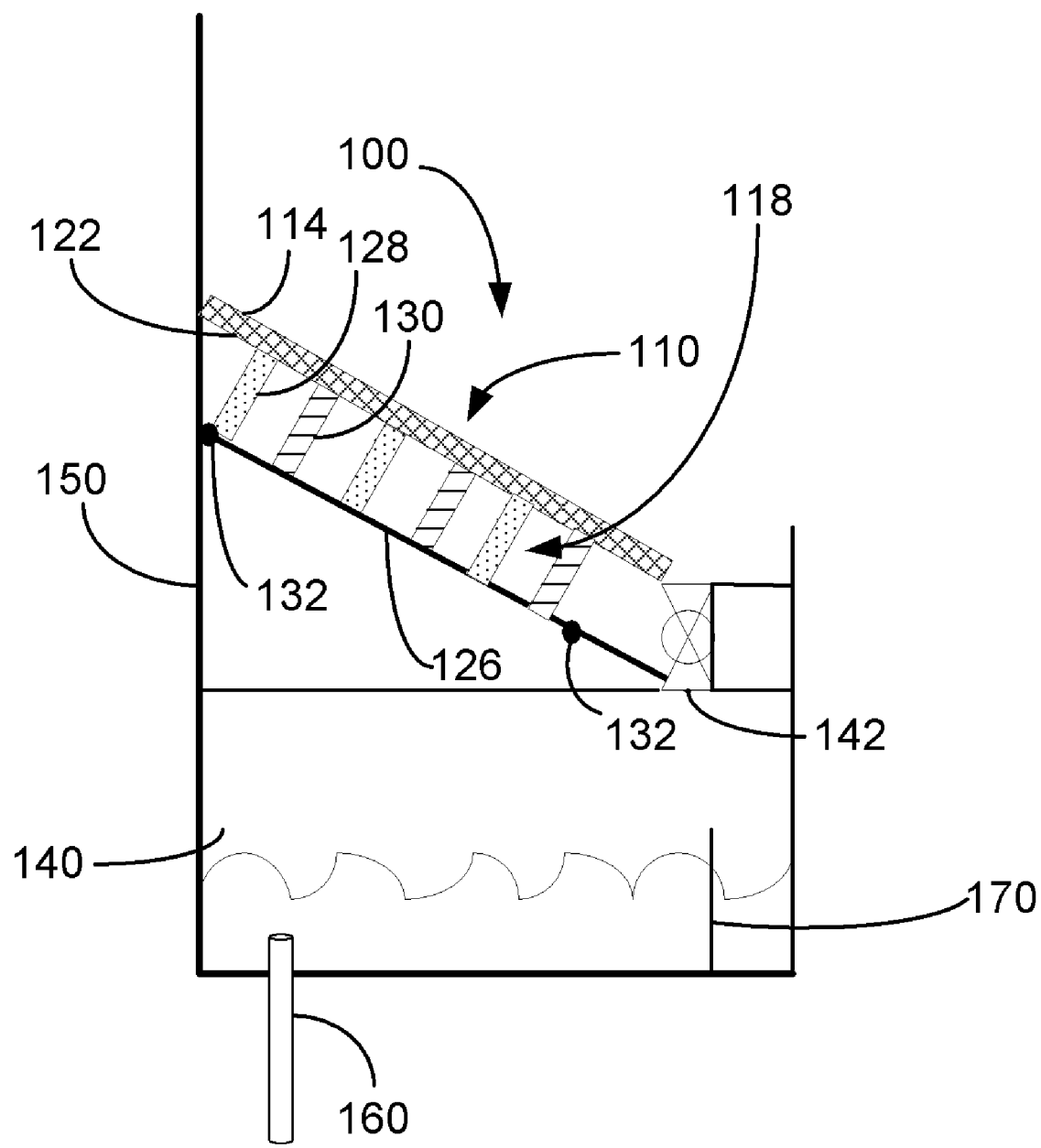
FIG. 1 is a schematic diagram of a condensation unit according to a disclosed embodiment.

FIG. 1 illustrates a condensation collector 100 according to an embodiment of the present disclosure. The condensation collector 100 includes a condensation unit 110, a collection vessel 140, a support 150, an extractor 160, and a liquid level meter 170. The condensation unit 110 is coupled to the support 150.

The condensation unit 110 includes a condensation surface 114. The condensation surface 114 is made of a material, or a coating on the material, that is conducive to condensation of a particular condensate, such as water. For example, when the condensate is water, a surface with high wettability, such as an optical surface, for example a mirrored surface, can be used as the condensation surface 114. In some examples, the material has a contact angle of less than 90° as measured by the tilting plate method. In more specific examples, the condensation surface 114 is a gradated material, having a range of contact angles that facilitate both condensation and transport of the condensate for collection.

In at least some implementations, the condensation surface 114 has a high thermal transfer coefficient, fairly efficiently transferring heat between opposing sides of the condensation surface 114. In some aspects, the material has a thermal conductivity of at least about 75 W/m·K, at least about 150 W/m·K, at least about 300 W/m·K, or at least about 400 W/m·K. In a particular example, the condensation surface 114 is metallic, such as polished aluminum, copper, silver, or alloys of such materials. In some implementations a high thermal conductivity metallic substrate is coated with Teflon or other material with a large wetted contact angle for water. Such a coating can promote the formation of droplets and subsequent removal of such droplets from the condensation surface 114 into the collection vessel 140.

The condensation surface 114 abuts a cooler 118, such as a Peltier or thermoelectric cooler. The Peltier cooler 118 is formed from a cold junction 122 and a hot junction 126. The cold junction 122 and hot junction 126 are separated by a series of alternating p semiconductors 128 and n semiconductors 130. The semiconductors 128, 130 are attached to wires 132 in communication with a power source (not shown). Application of a current to the semiconductors 128, 130 heats or cools the cold junction 122 and hot junction 126, depending on the direction of current flow. Suitable Peltier coolers 118 are available from Ferrotec (USA) Corporation of Bedford, N.H. However, other coolers can be used instead of, or in addition to, the Peltier cooler 118.

For example, the cooler 118 may include a cryogenic device or closed-cycle gas-expansion device. A particular implementation of a cryogenic device uses a liquid nitrogen or oxygen dewar as the cold source. A particular implementation of a closed-cycle, gas-expansion device employs compressed ammonia, or other suitable working fluid, to cool a condensation surface.

The condensation surface 114 includes, or is operatively associated or in contact with, a valve 142. Any suitable valve can be used, including ball valves, butterfly valves, control valves, gate valves, and needle valves. The valve 142, in some examples, is connected to an actuator (not shown), such as an electric motor or a solenoid in order to actuate the valve. The actuator may be in communication with a controller (not shown), such as those available from Ferrotec (USA) Corporation of Bedford, N.H.

In operation, such as to condense water from a vapor sample, a controller (not shown) activates the cooler 118, such as by applying a current to a Peltier cooler, causing the condensation surface 114 to cool. Fluid, such as water from surrounding vapor, condenses on the condensation surface 114. When a sufficient amount of fluid, illustrated with reference to water, has condensed on the condensation surface 114, the water flows into the collection vessel 140 through the valve 142. When the valve 142 is automatically controlled, the valve can be actuated prior to collection by sending a signal to the valve 142 to the controller and subsequently closed.

In further embodiments, current flow through the semiconductors 128, 130 is reversed, causing the condensation surface 114 to heat. Heating the condensation surface 114 helps the water collected on the condensation surface 114 to flow into the collection vessel 140. In particular embodiments, a controller (not shown in FIG. 1), available from Ferrotec (USA), controls collection of water over a period of time, periodically reversing current flow in order to collect accumulated water until a desired sample level has been reached. The valve 142 can be actuated to coincide with the current reversal, such as actuating the valve 142 when the current is reversed or after current reversal.

The liquid level meter 170 is used, in particular embodiments, to determine when a desired amount of condensate, such as water, has been collected. Once the desired amount of condensate has been collected in the collection vessel 140, the sample can be extracted by the extractor 160. In particular examples, the extractor 160 is a needle, such as a needle attached to a syringe or other conduit, such as a section of tubing. The sample thus can be transferred to a detector for testing.

Figure 2:
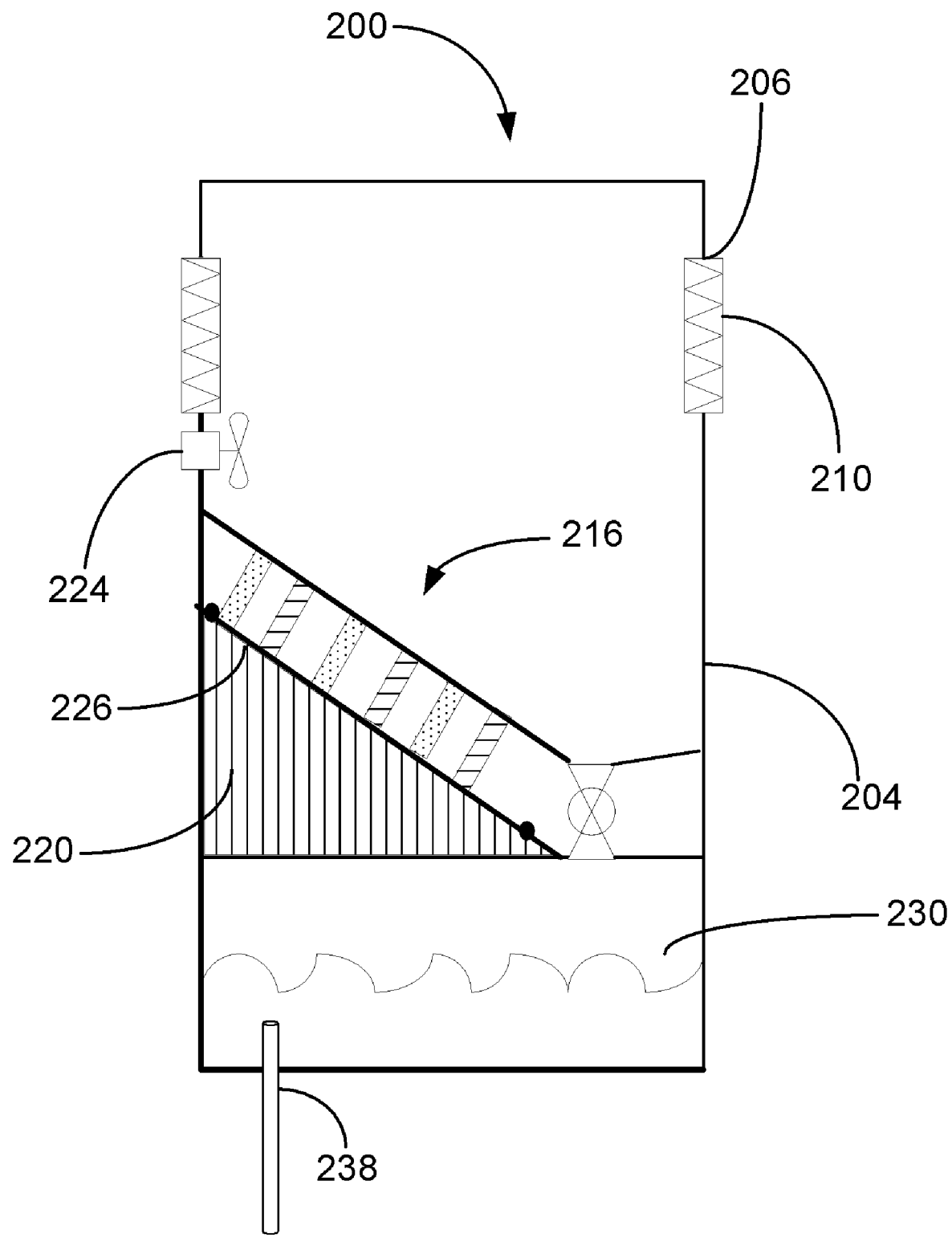
FIG. 2 is a schematic diagram of a condensation unit according to FIG. 1 configured for use in a detection device.

FIG. 2 presents an embodiment 200 of a condensation collection unit that can be included in a detection device, such as a detection device deployable in a well, which may be a test well. The collection unit 200 includes a housing 204 and an aperture 206 in the housing 204. In some examples, the housing 204 is cylindrical and constructed from stainless steel. However, the housing 204 may be shaped differently or constructed from other materials.

The aperture 206 is covered by a screen or filter 210. However, the screen or filter is omitted in some implementations. The aperture 206 may be of sufficient area to provide suitable passage for water vapor by diffusion alone. A condensation unit 216 is coupled to the housing 204. The condensation unit 216 may be constructed in an analogous manner to the condensation unit 110 of FIG. 1.

The condensation unit 216, particularly the hot surface 226 of the unit 216 (such as the hot junction 126 of FIG. 1), is thermally coupled to a heat sink 220, such as a mass of conducting metal, such as copper. The heat sink 220 is, in some configurations, thermally coupled to housing 204, which can aid in shedding heat from the condensation unit 216, thus potentially improving performance. Other heat sinks 220 can be used. For example, in another implementation, the condensation unit 216 is positioned vertically such that the heated surface of the condensation unit 216 is in contact with a vertical wall of the housing 204. Fans or radiative devices may also be used for the heat sink 220. In some implementations, the heat sink 216 is omitted or located elsewhere on the unit 200.

A fan 224 is located in the collection unit 200 to promote circulation of water vapor from the borehole into the condensation collection unit 200. In some implementations the fan 224 is omitted or located elsewhere.

An extractor 238 extends from the collection vessel 230. In some implementations, the extractor 238 is omitted.

In operation, fluid, such as air, from an area to be sampled enters the unit 200 through the screen 210 by diffusion or may be facilitated by the fan 224. Fluid condenses on the condensation unit 216 and is subsequently collected by the collection vessel 230. The fan 224 also serves to cool the hot junction of the condensation unit 216, improving the performance of the condensation unit 216. The extractor 238 removes all or a desired portion of the collected condensate from the condensation unit 200, such as transferring the condensate to a detector.

Figure 3:
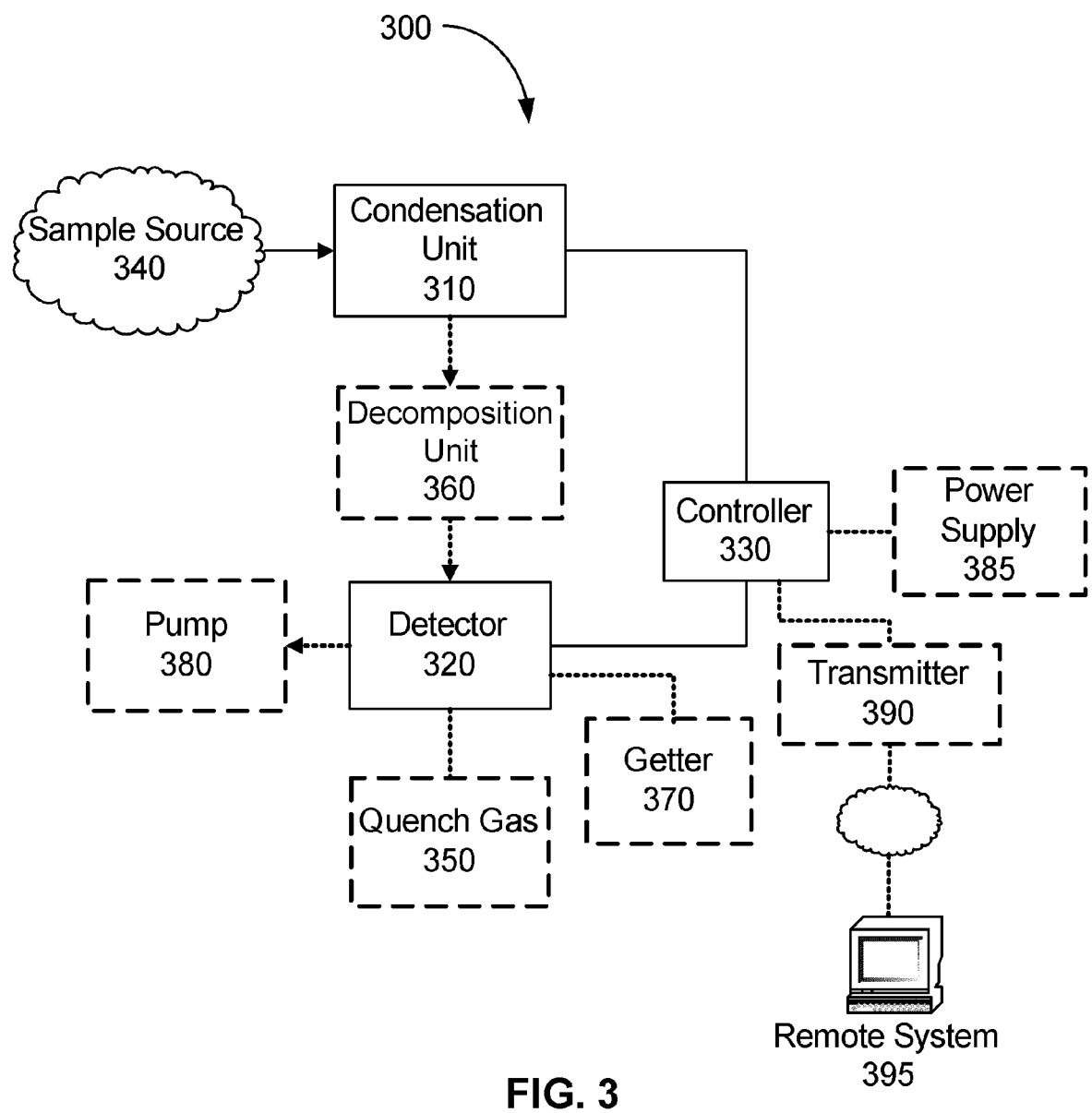
FIG. 3 is a block diagram of a radiation monitoring apparatus according to an aspect of the present disclosure.

FIG. 3 is a schematic diagram of a monitoring system 300. The monitoring system 300 includes a condensation unit 310, such as condensation unit 100 or 200. The condensation unit 310 is in communication with a detector 320 and a controller 330. The detector 320 may be any detector suitable for detecting a component of interest in the sample. In particular examples, the detector 320 is a proportional detector. Suitable proportional detectors are described later in this disclosure.

A sample from a sample source 340 may be transferred to the detector 320 by any suitable means. For example, the sample can be transferred by syringe or tubing. In particular examples, the syringe is a mechanical syringe. The syringe or tubing, in some configurations, is effectively coupled to a pump (not shown) or solenoid (not shown) to draw sample from the condensation unit 310 or push sample into the detector 320. In further examples, the sample is transferred to the detector 320 by a gravity fed mechanism. Some implementations include a flow meter or other device (not shown) to measure the amount of sample transferred to the detector 320.

In particular implementations, the system 300 is a radiation detection system, such as for monitoring tritium. When the system 300 is used for monitoring tritium, the detector 320 may be a liquid scintillation detector, a gas scintillation detector, or a proportional detector. Such detectors are commercially available. For example, a suitable proportional detector is available from Ludlum Measurements, Inc., of Sweetwater, Tex. In addition, the present disclosure provides proportional detectors useable in the system 300. When the detector 320 is a proportional detector, the system 300 typically includes a quench gas source 350 for the proportional detector 320. The quench gas may be any suitable quench gas for use in a proportional detector. Typical quench gasses include low molecular weight organic compounds, such as methane and propane.

The controller 330 is used to control the operation of the condensation unit 310 and the detector 320. Suitable controllers 330 are available from Mount Sopris Instruments of Golden, Colo. and from Ferrotech (USA).

In some implementations, the detector 320 analyzes a gaseous sample, such as analyzing $H_2$ and $^3H_2$. In certain such implementations, the system 300 includes a sample decomposition unit 360. In some examples, the decomposition unit 360 decomposes an aqueous sample into hydrogen (or tritium) gas by reacting a water sample with an active metal or metal alloy, such as Na, K, Li, or Ca. In a particular example, the water sample is reacted with an alloy of sodium and potassium, NaK. In a specific example, the alloy is 78% potassium and 22% sodium. In further examples the sample is decomposed electrically, such as by electrolysis of a water sample.

Some embodiments of the system 300 include a getter unit 370. The getter unit 370 contains an absorbent (or gettering) material to absorb a component that would otherwise interfere with sample detection. For example, when tritium is to be detected by the system 300, the gettering material can absorb hydrogen and tritium, such as tritium and hydrogen remaining from a prior test. In such cases, the gettering material can be a metallic or polymeric getter.

In some configurations, the system 300 is designed to be used in a remote environment. A pump 380 is used to draw quench gas 350, or other purge gas, through the system 300, including the decomposition unit 360 and the detector 320. When the detector 320 is not a proportional detector, or similar detector, any suitable inert gas can be used, such as nitrogen, helium, or argon. Drawing gas through the system 300 is used, in some examples, to remove contaminants, such as prior samples, from the system 300. In some embodiments, the pump 380 is omitted, and the getter unit 370 is included.

The system 300 also includes, in particular implementations, a power supply 385 in communication with the controller 330. The power supply 385 may be, for example, batteries, such as deep cycle batteries, or a solar panel. Although FIG. 3 illustrates power being transferred from the controller 330 to the other components of the system 300, power is transferred to directly to such components from the power supply 385 in further implementations.

The system 300 is shown with a transmitter 390. The transmitter 390, which is omitted in some embodiments, is in communication with a remote system 395, such as through the internet. The transmitter 390 may be a wireless transmitter or a wired connection, such as being connected to a cable, power line, or phone line.

The transmitter 390 allows data, and system performance, to be monitored or controlled by a remote user. Remote monitoring and control can be particularly important when the system 300 is located in a remote or inaccessible location, or when large numbers of monitoring sites make physical inspection of the system 300 impracticable.

The described systems and apparatus may be used in a variety of ways. For example, because the described systems can be constructed to be relatively compact, and are capable of sensitive detection using condensed air, they can be deployed near test sites of interest, such as sites of suspected nuclear activity. In some examples, the instrument is carried in a vehicle, left in a structure near the test site, or otherwise inconspicuously placed in position to monitor the area of interest.

In addition to atmospheric monitoring, embodiments of the present disclosure can be used to monitor subsurface vapor, such as subsurface vapor phase tritium plumes. Such plumes are present in sites such as Beatty, Nev., and Rocky Flats, Colo. In particular examples, the disclosed monitoring devices are used to detect vapor phase tritium occurring between the ground and the water table.

Although specific embodiments of the present disclosure have been described with reference to tritium monitoring, the present disclosure is not so limited. Particular embodiments of the present disclosure may be used in monitoring applications where a component of interest in a vapor is condensable by cooling. In one particular example, the disclosed systems are used to detect petrochemical plumes. In a more specific example, long chain hydrocarbons present in a vapor sample are condensed and detected. For example, this method may be used to detect leaking gasoline storage tanks.

The described systems and apparatus may provide a number of advantages. For example, a smaller amount of air is needed to produce a suitable sample compared to many prior techniques. Therefore, active pumping is not needed, and a suitable sample can be obtained from the air surrounding the instrument. Accordingly, the sample produced by the disclosed systems may be more representative of the area of interest. In other words, the disclosed systems can provide greater positional accuracy. However, the disclosed systems and apparatus may be used with active pumping, if desired.

In particular methods, the disclosed systems are used to investigate a zone of interest in a well bore or similar structure. A particular zone of interest can be isolated using packers. The use of packers, or similar devices, helps ensure that the sample obtained is representative of the area of interest.

Figure 4:
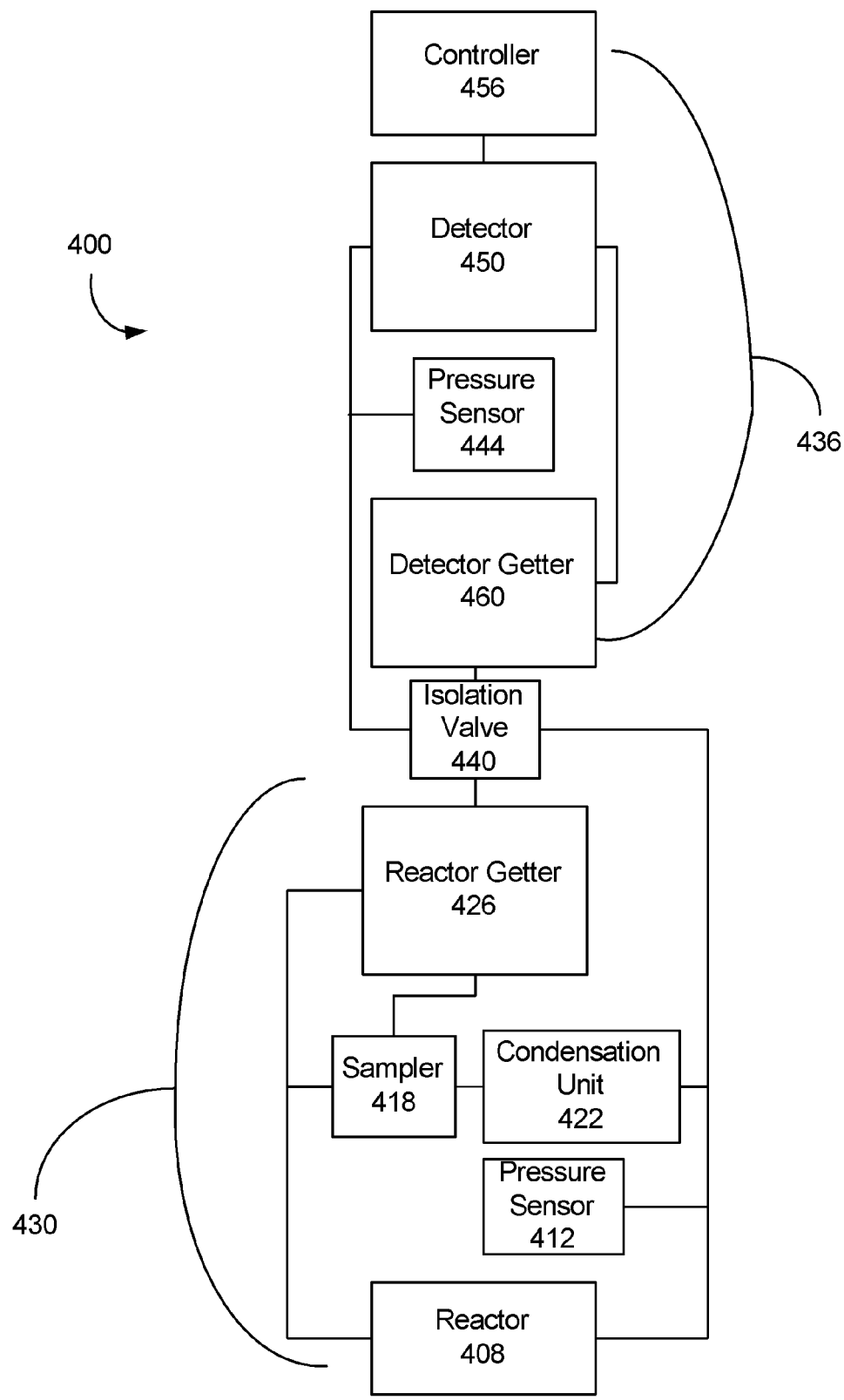
FIG. 4 is a schematic diagram of a radiation monitoring apparatus according to an aspect of the present disclosure.

FIG. 4 presents a schematic diagram of components that may be included in various embodiments of a radiation monitoring device 400 according to the present disclosure that includes a condensation unit. Starting at the bottom of FIG. 4, a reactor 408 is in communication with a pressure sensor 412, such as a strain gauge type pressure sensor. The reactor 408 is also in communication with a sampling device 418. The sampling device 418 is omitted in some examples. The sampling device is in communication with a condensation unit 422. The pressure sensor 412, reactor 408, sampling device 418, and, optionally, the condensation unit 422, are in communication with a reactor hydrogen getter 426. The pressure sensor 412, reactor 408, sampling device 418, condensation unit 422, and reactor hydrogen getter 426 form a reactor portion 430 of the instrument 400.

A detector portion 436 of the instrument 400 is separated from the reactor portion 430 by an isolation valve 440. The detector portion 436 of the instrument 400 includes a pressure sensor 444 in communication with a detector 450. The detector 450 is in communication with a controller 456. The detector portion 436 includes a detector hydrogen getter 460 in communication with the detector 450. The components of the device 400 may be placed in communication with one another using suitable tubing or piping, such as stainless steel piping or may be directly connected and separated by valves or similar means.

Instruments according to the present disclosure need not include all of the components shown in FIG. 4 or have the components in the same order or location. For example, the isolation valve 440 is omitted in certain implementations. In further examples, the pressure sensors 412, 444 are omitted and, optionally, replaced by flow meters or other sensors. The disclosed instruments also may include additional components.

In operation, the condensation unit 422 condenses a vapor sample, such as from a particular section of a well bore, into a liquid sample. The sample is then transferred from the condensation unit 422 to the sampling device 418. The sample is injected from the sampling device 418 into the reactor 408. The reactor 408 converts the sample into a form suitable for use in the detector 450. In a particular implementation, the reactor 408 decomposes an aqueous sample into one or more gaseous components, such as hydrogen, and other reaction products. For example a sample of tritiated water condensed from a vapor sample may be converted to hydrogen gas, tritium gas, and oxides.

Gas formed in the reactor 408 is transferred by the pressure sensor 412 to the detector 450 through the isolation valve 440. The pressure sensor 412 can be used to determine the amount of gas generated by the reactor 408. Knowing the volume of gas generated allows the amount of sample to be accurately determined, such as from the ideal gas law. The volume of gas can also be measured before the sample enters the detector 450, such as by the pressure sensor 444.

The reactor hydrogen getter 426 is used to remove, or sequester, hydrogen generated by the reactor 408 from the components of the reactor portion 430. Hydrogen removal helps to ensure that a particular test measures only the gas produced by the sample, not residual hydrogen and tritium that may otherwise remain in the instrument 400 from a previous test.

The isolation valve 440 separates the reactor portion 430 from the detector portion 436. Separating the reactor portion 430 from the detector portion 436, along with the use of a separate detector hydrogen getter 460, may facilitate clearing prior samples, such as hydrogen and tritium gas, from the device. In addition, separating various getters in the instrument 400 may allow different getter materials to be used in different portions of the instrument 400. In one particular implementation, isolating the reactor getter 426 from the detector portion 436 during detection allows a less expensive or efficient gettering material to be used in the reactor getter 426. Isolating the reactor getter 426 from the detector portion 436 may also allow getter material to be used that would otherwise be incompatible with the detector portion 436, such as with a quench gas.

The detector 450 detects one or more components of interest, such as tritium gas. In particular examples, the detector 450 includes a quench gas, such as when the detector 450 is a proportional detector. The quench gas is typically an organic compound, such as propane or methane, a mixture of organic compounds, or an inorganic gas. The quench gas, in some examples, is initially dosed to the instrument 400 through a fill valve (FIG. 6, 610) prior to the instrument 400 being deployed for testing. To help prevent interaction between the metal alloy of the decomposition unit 360 (FIG. 3) and the quench gas, the isolation valve 440 can be included to help preclude the transport of quench gas from the detector portion 436 to the reactor portion 430.

The detector 450 is in communication with the controller 456. The controller 456 may be used to operate the instrument 400, perform data analysis, collection, or manipulation or to communicate with a user, such as a remote user, or remote systems.

The present disclosure is not limited to the configuration of FIG. 4. For example, certain embodiments do not include one or more of the components shown in FIG. 4, such as the isolation valve 440, separate reactor 426 and detector 450 getters, or pressure sensors 412, 444. The device 400 can include additional components, such as additional detectors for detecting other sample components, such as sensors to quantify organic or inorganic compounds present in a sample. In some configurations, the sampler 418 obtains samples from sources in addition to the condenser unit 422. For example, the sampler 418, in particular examples, obtains liquid samples directly from a liquid source, such as water in a well bore.

Additionally, the controller 456 may be configured to communicate with other sensors, such as commercially available sensors including, but not limited to, sensors for pH, dissolved oxygen, specific ions, and total gamma radiation. In further implementations, the functions of multiple components may be combined in a single unit, such as a combined detector 450 and controller 456. The components of the apparatus 400 may be connected and arranged in a different manner than illustrated in FIG. 4. For example, the controller 456 may be located remotely from the remainder of the apparatus 400.

Figure 5:
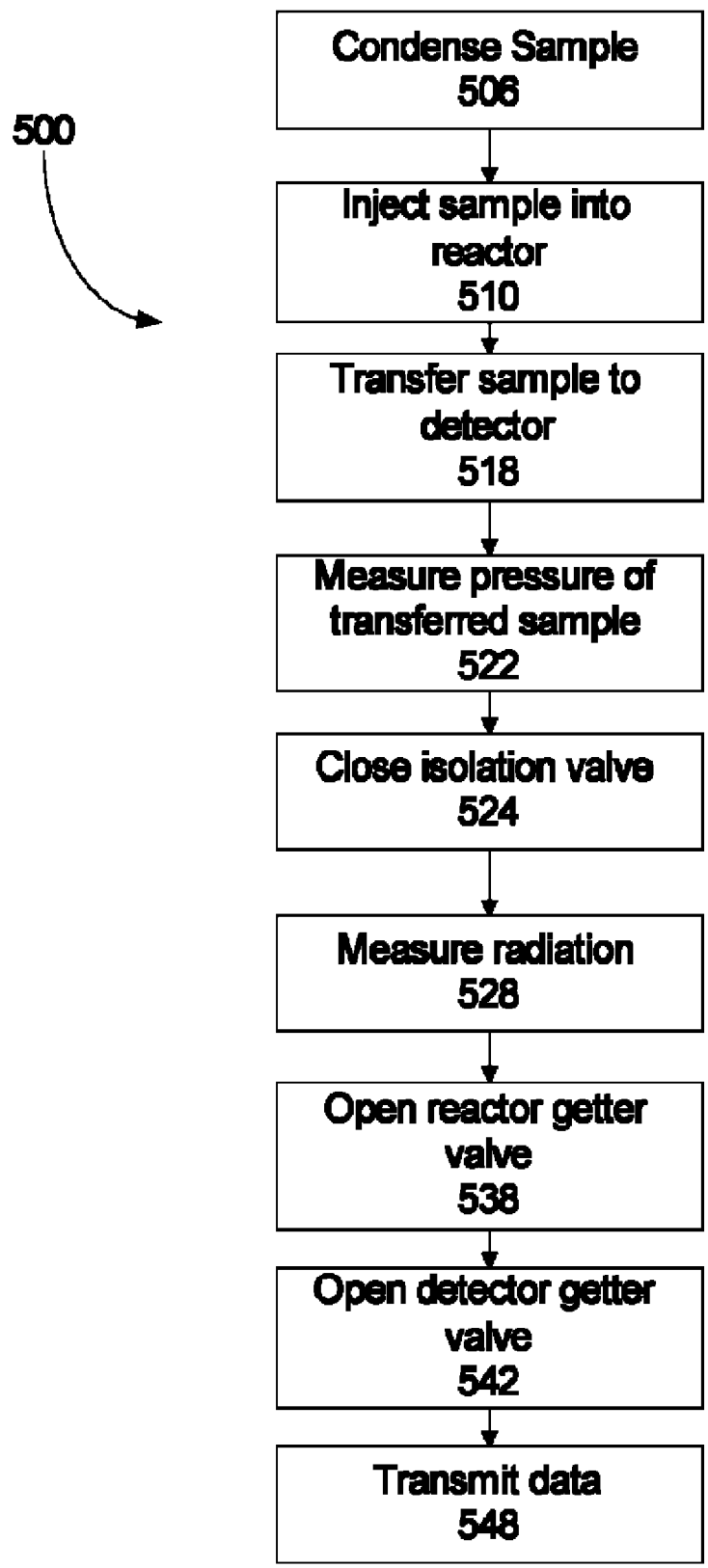
FIG. 5 is a flowchart of a method of operating the radiation monitoring apparatus of FIG. 4.

FIG. 5 presents a flowchart of a method 500 of operating the instrument 400 of FIG. 4 to detect tritium. At step 506, a vapor sample is condensed using the condensation unit 422. The condensed sample is introduced into the reactor 408 at step 510, such as using the sampler 418. In the reactor 408, the sample may be converted to a form suitable for use in the detector 450, such as a gas. At step 518, the sample is transferred to the detector 450 through the isolation valve 440. At step 522, the pressure of the gas transferred to the detector 450 is measured by the pressure sensor 444. The mass of the generated gas is then calculated from the pressure measurement made by pressure sensor 444, such as by using the ideal gas law and the known volume of the detector 450 and associated connections.

The isolation valve 440 is closed at step 524 when the pressure difference between the reactor pressure sensor 412 and the detector pressure sensor 444 has achieved a certain positive value, thereby ensuring that gas has flowed from the reactor 408 to the detector 450. Pressure in the detector 450 is monitored and allowed to stabilize before applying voltage to the detector. The radioactivity of the sample is then quantified by the detector 450 and the controller 456 at step 528.

Typically while radiation is being detected at step 528, and while the isolation valve 440 is closed, the reactor getter valve is opened at step 538, allowing the remaining hydrogen-tritium gas sample to be removed from the reactor portion 430 of the instrument 400. The controller 456 operates the detector 450 until one or more statistical criteria, preset by the user, are met. Statistical criteria can include, but are not limited to, total counts, count average, count standard deviation and total count time. Other statistical criteria not specified here also may be used. Once detection has been completed, a valve to the detector getter 460 is opened at step 542, allowing sample to be removed from the detector portion 436 of the apparatus 400. Gettering proceeds until a certain pressure has been achieved in both the reactor portion 444 and the detector portion 430 as determined by monitoring the pressure sensors 412 and 444. In certain instances the residual pressure in the reactor portion 444 as measured by the pressure sensor 412 will be no or very little pressure, while in certain other instances the residual pressure in the detector portion 430 as determined by the pressure sensor 444 will be the partial pressure of the quench gas.

In step 548, the data recorded by the detector 450 is transmitted to a remote computer, such as to a surface computer and/or a remote computer, such as a monitoring center.

Figure 6:
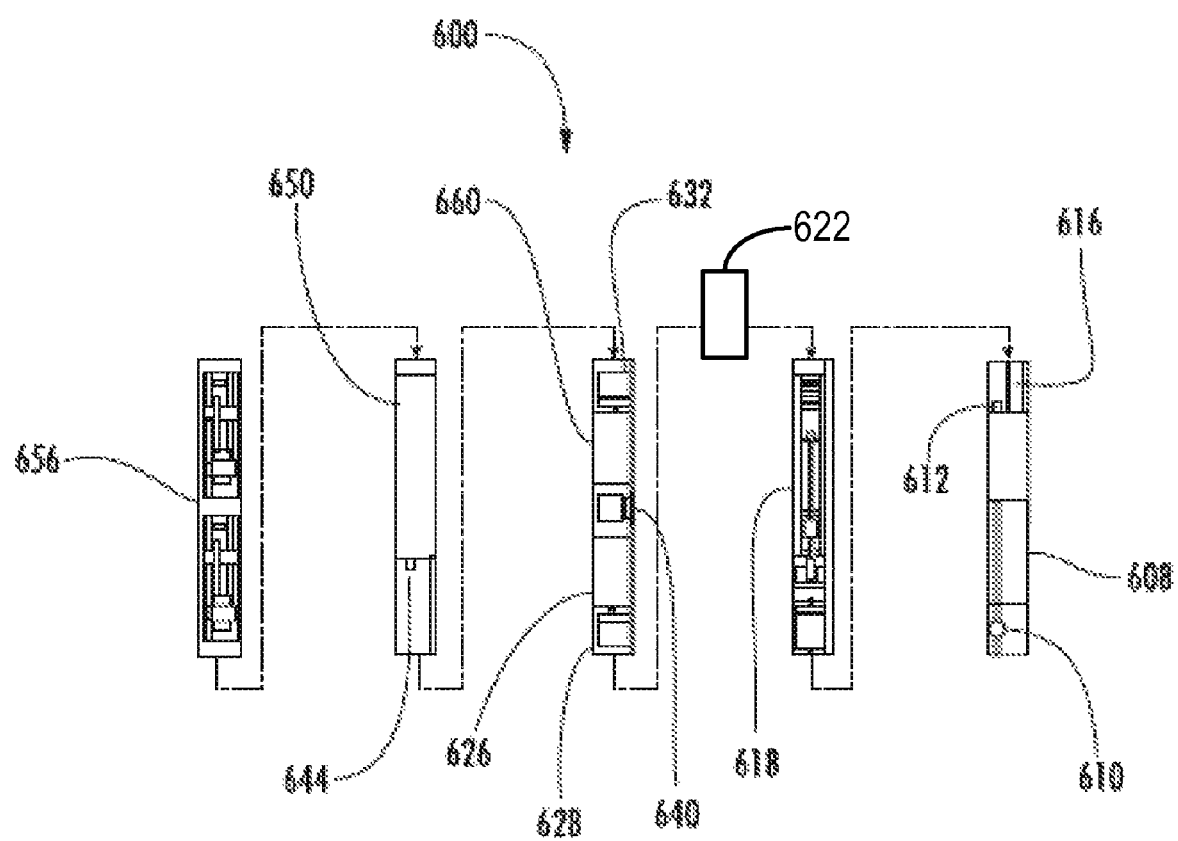
FIG. 6 is a schematic diagram of a particular radiation monitoring apparatus according to the embodiment of FIG. 4.

FIG. 6 presents a schematic diagram of a device 600 which is a particular implementation of the device 400 of FIG. 4. Components of the device 600 which correspond to components in the device 400 are correspondingly labeled (with reference numbers in the 600s). The condensation unit 622 is the condensation unit 200 of FIG. 2. The reactor 608 is connected to a valve 610 that may be used to evacuate the reactor 608 with a vacuum pump system, charge the reactor 608 with reactant or purge the reactor 608 with gas, as explained in more detail below. A liquid conduction line 616 connects the sampling device 618 with the reactor 608. A fluid conduction line (not shown) connects the reactor 608 with the reactor pressure sensor 612, the reactor getter 626, the detector 650, and the detector getter 660 with valves (not shown) controlling fluid flow to each of these components.

The sampling device 618 is configured to operate at the ambient temperatures and pressures in the environment in which the device 600 will be used. When used to measure tritium in a well bore, such pressures can range up to 1,800 psig or higher. In particular embodiments, the sampling device 618 is a mechanical syringe, such as a mechanical syringe with an adjustable stroke. In a specific example, the stroke of the mechanical syringe can be configured using two limit switches in communication with the controller 656. An adjustable stroke allows the volume of water obtained by the sampling device 618, and subsequently injected into the reactor 608, to be tuned to provide a desired sample volume. Suitable motorized syringes include those used in commercially available well logging injector tools.

Although the device 600 uses a syringe-based sampling device 618, any suitable sampling device can be used. In certain examples, the sampling device 618 is a free piston hydraulic machine, which in more specific examples is powered by the pressure difference between the borehole hydraulic head and the vacuum pressure within the reactor 608. This embodiment is particularly useful when the instrument 600 is deployed to depths in excess of a certain value, such as 100 m, because it does not require any additional power to operate, and can simplify the electro-mechanical aspects of the sampler 618. At shallower deployment depths, the pressure gradient between the borehole and the reactor portion 630 is typically not great enough to cause a water sample to flow into the reactor 608 to ensure complete reaction of the sample with the metal alloy, and the electro-mechanical syringe injector is therefore typically used. A sample may be transferred from the condensation unit 622 to the sampling unit 618 by a gravity feed mechanism. A flow meter (not shown) may be included to regulate the amount of sample transferred. In further specific examples, the sampling unit 618 is omitted and the sample is transferred directly from the condensation unit 622 to the reactor 608.

The reactor portion of the device 600 includes a reactor getter unit 626. The reactor getter unit 626 includes a valve 628 that can be selectively opened. The reactor getter can be any suitable shape and is typically sized to hold a desired amount of sample and getter material. In particular embodiments, the reactor getter unit is cylindrical and constructed from stainless steel. The getter material may be placed loose in the reactor getter 626 or may be placed in a permeable container. For example, the getter material may be placed in a sock of material. In further implementations, a gas permeable barrier is placed between the getter material and the remainder of the getter unit 626 to secure the getter material in the getter unit 626.

Any suitable hydrogen absorbing material can be used in the reactor getter unit 626. Two suitable types of getter material are metallic getter materials (various metal-oxide-based products, such as those described in U.S. Pat. No. 4,668,424) and polymeric getters, such as those having platinum bearing groups. Suitable polymeric getters are available from Sandia National Laboratories. One such class of materials is described in U.S. Pat. No. 7,001,535, incorporated by reference herein.

The getter material is chosen to remain active in the presence of gases to which the getter material will be exposed. For example, quench gasses such as propane or methane may poison certain metallic getters. In certain implementations, such as when an instrument is desired that can perform multiple tests before requiring maintenance, it may be desirable for the getter material to be regenerable.

When a measurement takes place, the valve 628 is closed, and the gas sample generated by the reactor 608 is transferred to the detector portion of the device 600 through the isolation valve 640. Once the generated sample gas has been transferred to the detector portion, the valve 628 is opened, allowing hydrogen gas in the reactor portion to be sequestered by the getter material.

The isolation valve 640 may be any suitable valve, and is typically in communication with, and controlled by, the controller 656. In particular examples, the isolation valve 640 is an electrically operated solenoid valve. Suitable valves are commercially available from Snap-Tite, Inc., of Erie, Pa., and may be magnetically-latching or non-latching valves. Magnetically latching valves are particularly suitable if the isolation valve 640 will be left open for extended periods of time.

Turning now to the detector portion, the detector getter 660 may be constructed in a manner similar to the reactor getter 626. A getter material is typically selected that will not be poisoned by the quench gas. For example, when the quench gas is organic, the getter material can be a polymeric getter material. Because it separates the detector portion, which contains a quench gas, from the reactor portion, which does not contain a quench gas, the isolation valve 640 allows less costly, potentially less efficient getter materials to be used in the reactor portion relative to that used in the detector portion. The isolation valve 640 also allows the getter material in the reactor portion to remove hydrogen while detection is taking place in the detector portion, potentially a significant amount of time. Providing a longer time for removing hydrogen may allow a wider variety of getter materials to be used. Like the reactor getter unit 626, the detector getter unit 660 includes a valve 632 that can be selectively opened and closed to allow the getter unit 660 to be placed in fluid communication with the remainder of the detector portion.

A pressure sensor 644 is positioned intermediate the detector 650 and the isolation valve 640 in the sample flow path. The pressure sensor 644 allows the quantity of sample gas reaching the detector 650 to be measured by the controller 656.

The detector 650 may be any suitable detector, such as a gas scintillator detector or a proportional detector. The detector 650 is typically constructed to operate at the ambient conditions, including potentially high pressures and temperatures that may be encountered when the instrument 600 is in use.

Controller

The controller 656 includes a microprocessor that communicates with a remote system (not shown). In particular examples, the controller 656 is a microprocessor operable in a down-hole environment and the remote system is a surface module incorporating features such as an additional microprocessor, communications equipment, batteries, or solar panels. Suitable controllers 656, and remote systems, may be obtained from Campbell Scientific, Inc., of Logan, Utah. The CSI 1000 controller is one such suitable device.

The controller 656 and surface module may be placed in communication using a cable, such as an armored multiconductor steel cable of the sort used by geophysical borehole logging equipment. The controller 656 communicates with the surface module via the cable using a complex command script transmitted via standard RS232 protocol. However, other protocols may be used. The controller 656 is configured to operate the valves of the instrument 600, such as the isolation valve 640, the detector getter purge valve 632, and the reactor getter valve 628. The controller 656 also powers the detector 650 and collects the signal from the detector 650. The operation of the condensation unit 622 is also controlled by the controller 656.

In particular examples, the controller 656 includes separately addressable sections or circuit boards; including one or more modem/microprocessor boards, solenoid boards, and spectrometer boards. Information from the surface module is received by the modem/microprocessor board, interpreted by the controller 656, which in turn passes on commands to the appropriate board. The surface module may also issue commands to query information stored in the controller 656, such as pressure and temperature readings from the reactor 608 or detector 650, cycling information from the motorized syringe and rotary inlet valve, and counts from the spectrometer board.

In this example, each solenoid board is capable of controlling 4 latching DC solenoids and has measurement input channels for a pressure transducer and a thermister temperature sensor. A pulse of positive polarity supplied to a solenoid magnetically latches the value to an open position; conversely, a pulse of negative polarity to the solenoid returns the valve to a normally closed position.

Power is supplied the device 600 from land surface via a surface module, such as from solar panels, batteries, or an AC line source. The surface module supplies DC voltage to the wireline that serves as both the mechanical support and means of communication with the device 600. A voltage regulator board co-located with the controller 656 distributes incoming power from the surface module to the various electrical components of device 600. In the embodiment described in FIG. 6, these components include +/−3 VDC to solenoids, +/−50 VDC to the motorized components, and +14 VDC to the controller 656. In addition, the controller 656 has a 12 VDC sealed lead acid battery that acts as a buffer against voltage variations from the surface module.

The spectrometer board supplies high voltage to the detector 650 and amplifies and counts low voltage pulses produced by tritium disintegrations in the detector 650. The high voltage power supply is software controllable from 0 to 5000 volt DC, in $(256)^2$ increments (5000 volts divided by 65536 increments=76 millivolts resolution). Pulses from the detector 650 are counted in 256 spectral energy bins. Each energy bin is capable of accumulating up to 65536 counts ($256^2$) before the bin is full, at which time the bin will overflow and no more pulses will be counted. The energy bin threshold and span are software controllable and therefore can be adjusted to a small energy window specific to tritium, or can be adjusted to a broader window, such as for measuring tritium and radon.

Sample Reactor

As explained above, the disclosed devices, such as the devices 400 or 600, may be designed to detect tritium, which emits a low energy β-particle (18.6 KeV). This energy is so low that the emitted β-particle is absorbed even by air. Rather than a detector with a window, which may be impenetrable to the β-particles, at least certain disclosed devices are designed to place tritium in intimate contact with the detector, such as in the above-described scintillation and proportional detection systems.

One method of placing tritium in intimate contact with a detector is to convert the tritium in water, including water condensed from a vapor sample, to $^3H_2$ gas. Detecting radiation in gas can have advantages over aqueous detection systems. First, hydrogen-tritium mixtures typically will be devoid of $^{14}C$, $^{40}K$, $^{238}U$ or any other radioactive isotope (except $^{226}Rn$, which is gaseous). Second, hydrogen-tritium mixtures can be passed through activated carbon to remove up to 99.9 percent of the radon. The remaining radon activity can be separately counted because of the large energy difference between it (6,000 KeV) and tritium (18.6 KeV). Tritium can be counted after waiting a relatively short period of time after gas formation to allow the very short half-life of radon to lower the activity of radon to below detectable levels. Alternatively, the activated carbon filter can be omitted and radon can be excluded from measurements by waiting until the radon naturally decays. The use of purified hydrogen/tritium gas can thus greatly minimize the background radiation admitted into the detector 650 and allow relatively low levels of tritium to be detected.

Any suitable method can be used for decomposing water into hydrogen (or tritium) gas. One method uses electrolysis to reduce the $H^+$ ion of water into elemental hydrogen, $H_2$, and oxidizes the $O^{2-}$ into elemental oxygen, $O_2$. Another method uses chemical reactions, such as reaction with active metals including, without limitation, sodium, potassium, lithium, calcium, metal alloys, or combinations thereof, to decompose water into hydrogen and metal hydroxide.

Elemental sodium and potassium can be combined to form a eutectic alloy that is molten at room temperature. This alloy is commercially available from BASF Corporation of Florham Park, N.J., in the ratio of 78 percent potassium and 22 percent sodium, and is referred to as NaK. Since it is a liquid, NaK can be relatively easily transferred into the reactor 608, such as by pumping the NaK into the water decomposition reactor 608.

Figure 7:
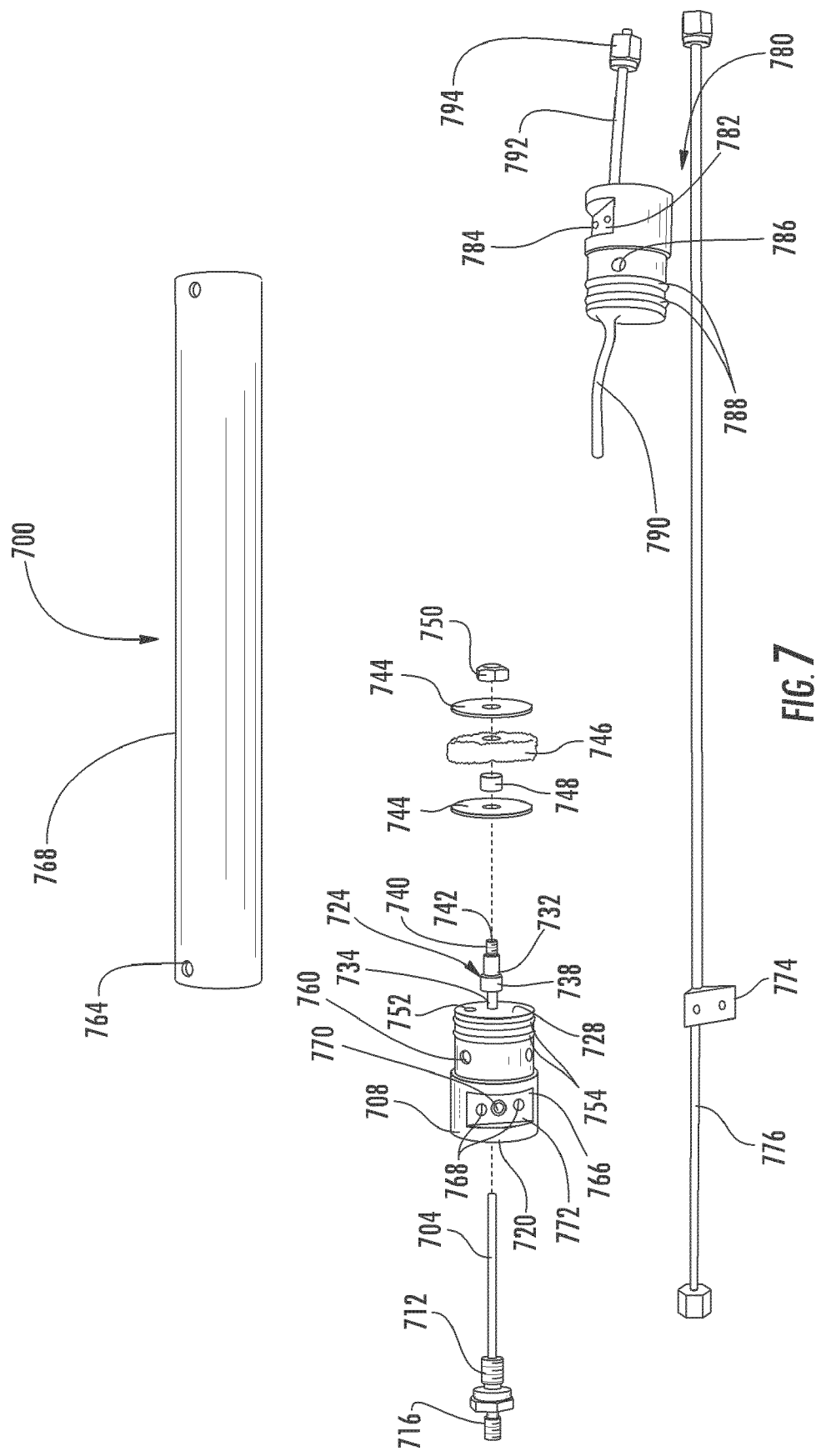
FIG. 7 illustrates a water decomposition reactor useable in the radiation monitoring apparatus of FIG. 4.

The reactor 700 shown in FIG. 7 is suitable for reacting a liquid sample with NaK in a remote setting. A removable needle 704 is insertable into the top end 708 of the reactor 700. The removable needle 704 may be secured by a threaded barrel 712 received by mating threads of a bore (not shown) formed in the outer surface 720 of the top end 708 of the reactor 700. A smaller diameter threaded barrel 716 extends opposite the threaded barrel 712 and may be used to connect the reactor 700 to other components, such as a sample source. For example, the threaded barrel 712 may connect the reactor 700 to the sampling device 418, 618.

A hollow shaft 724 of a baffle structure extends perpendicularly from an inner surface 728 of the top end 708. The shaft 724 includes a generally frustoconical portion 732 which abuts a narrow portion 734 of the shaft 724 proximate the inner surface 728. The frustoconical portion 732 has a larger diameter end 738 and a threaded portion 740 intermediate the end 738 and an outer end 742 of the frustoconical portion 732.

Two washers 744 are placed over the frustoconical portion 732 of the shaft 724. Bronze or stainless wool 746, or similar substantially non-reactive material, is placed between the washers 744. The wool 746, when mounted on the shaft 724 with a spacer 748 and nut 750, serves to help prevent material other than the gas sample from entering an aperture 752 formed on the inner surface 728. The aperture 752 is located approximately midway on the radius of the inner surface 728.

Two circumferal channels (not shown) are formed in the side of the first end 708 of the reactor 700. Each channel may be fitted with an O-ring 754. The O-rings 754 may be made from any suitable material, which are typically resilient and non-reactive towards materials commonly used with the apparatus, such as water, NaK, heat, and the mineral byproducts of the reaction of water and NaK. In particular examples, the O-rings 754 are formed from rubber or another polymer. In a more particular example, the O-rings 754 are buna-n O-rings. The O-rings 754 are typically selected to be of a size to provide a tight seal between the first end 708 of the reactor 700 and the remainder of the reactor 700.

A plurality of threaded bores 760 are formed in a side wall of the first end 708 of the reactor 700. The threaded bores 760 are configured to receive matingly fitted screws (not shown) inserted through apertures 764 formed in the reactor body 768. Three rectangular depressions 766 are formed in the outer end of the first end 708 of the reactor 700. Two threaded bores 768 are formed in each of the rectangular depressions 766. The threaded bores 768 may receive matingly threaded screws (not shown). The screws may be used to attach the reactor 700 to other components of a radiation monitoring device, such as the radiation monitoring device 400 or 600, such as a gas manifold (described further below).

In a particular example, one rectangular depression 766 has a central aperture 770 in fluid communication with the aperture 752 of the inner surface 728. The aperture 770 is surrounded by a channel that receives an o-ring 772. The o-ring 772 may be selected as described for o-rings 754. In other examples, another rectangular depression 764 has an aperture (not shown) in communication with an aperture if the end 742 of the shaft 724.

The top end 708 of the reactor is attachable to one or more gas manifold assemblies 774. Each gas manifold assembly 774 includes a passage for transferring gas between the reactor 700, an assembly 774, and other portions of a monitoring instrument. Gas transfer tubing 776, which is made of stainless steel in some examples, is attached to the manifold 774. Monitoring instruments according to the present disclosure can use other assemblies, such as a manifold block having a solenoid valve and a T-joint. In other implementations, an end fitting of the reactor 700 serves as the base for the solenoid valve. Fasteners used to secure the manifold to the fitting may have passages or bores to allow gas to be transferred to or from the reactor.

A number of rectangular depressions 782 are formed in a lower end 780 of the reactor 700. Two threaded bores 784 are formed in each of the rectangular depressions 782. Matingly threaded screws (not shown) may be inserted into the threaded bores 784 to secure the lower end 780 to other components of the reactor 700. A plurality of threaded bores 786 are formed in the side of the lower end 780. Matingly threaded screws (not shown) may be inserted into the threaded bores 786 to secure the lower end 780 to the reactor body 768. A plurality of channels (not shown) are formed in the side of the lower end 780. O-rings 788 are placed in the channels and may be selected as described for O-rings 754.

A pipe 790 having a slight s-curve towards its middle extends outwardly from an inner surface of the lower end 780. The pipe 790 is in fluid communication with a pipe 792 extending from the outer end of the lower end 780. In particular implementations the pipe 792 is the same as the pipe 790. The pipe 792 includes a fitting 794 for attachment to other components of a device 400, 600.

The reactor 700 operates as follows. A quantity of NaK is pumped into the pipe 792. The amount of NaK introduced into the reactor 700 is greater than the volume of the reactor below the top of the pipe 790. An inert gas, such as argon, is then introduced into the reactor 700, such as through the manifold 774, to push NaK above the level of the pipe 790 through the pipe 790. Bubbles of the gas appearing in the NaK removed from the reactor 700 indicate that the NaK level in the reactor 700 is even with the top of the pipe 790. Although other methods of introducing NaK into the reactor may be used, this disclosed method allows a known quantity of NaK to be accurately and conveniently introduced into the reactor 700.

When a radiation measurement is to be obtained, a quantity of sample is injected into the reactor 700 through the needle 704. The sample is injected with sufficient force to break through the surface of the NaK layer, ensuring that the sample contacts active NaK, rather than other materials, such as mineral products, that may be present on the surface of the NaK. The needle 704 may be chosen to be of a gauge suitable for achieving the desired sample velocity once in the reactor 700. In a particular example, the needle is a 22 gauge needle.

The reaction of the sample with NaK produces metal oxides and hydrogen and tritium gas. Gas generated from the reaction passes through the aperture 752 in the inner surface 728 of the upper end 708 and through the aperture 770 formed in the rectangular depression 766. The shaft 724, including the washers 744 and bronze wool 746, at least partially cover the aperture 752. The wool 746 helps prevent NaK, metal oxides, and other materials from being transported to other components of the instrument 400, 600, aiding in preventing corrosion and contamination, and potentially reducing maintenance. Locating the needle 704 inside the hollow shaft 724 similarly helps prevent material from depositing on and possible damaging or obstructing the needle 704.

The components of the reactor 700 are constructed from suitably strong, inert materials, such as stainless steel. The reactor 700 is constructed to withstand operating temperatures, pressure, and moistures encountered by the apparatus 400, 600. The reactor 700 is also constructed to withstand the pressures generated by the reaction of the sample with the NaK, as well as be relatively inert to NaK, moisture, and NaK reaction products. The reactor 700 is dimensioned to provide a suitably sized space to promote the reaction of the sample with the NaK, generate a desired pressure upon reaction of the NaK with the sample, and hold a quantity of NaK sufficient to perform a desired number of measurements before maintenance on the reactor 700 is needed, such as emptying the reactor 700 and recharging it with a quantity of NaK.

Figure 9:
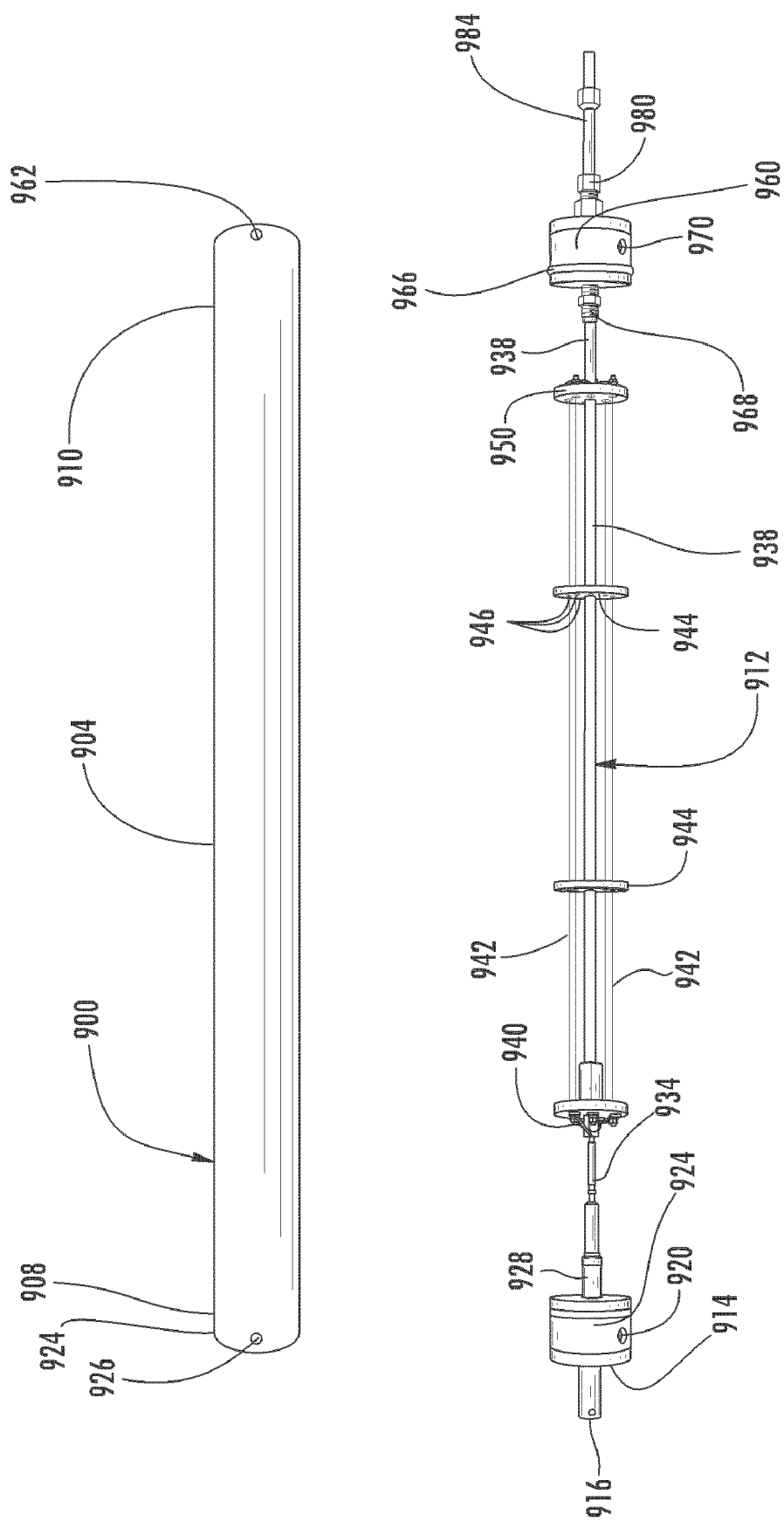
FIG. 9 illustrates a proportional detector for use with various disclosed embodiments, including in the radiation monitoring apparatus of FIG. 4.

Two valves (not shown) located at the bottom of the reactor 700 are used to prepare the instrument 600 for operation. These valves are used to transport gaseous components, and NaK. A gas transfer valve is used to evacuate the device 600 to remove atmospheric gases, including water vapor, such as using a high-vacuum pumping system (not shown). The gas transfer valve is also used to dose the quench gas to the detector (FIG. 9). The isolation valve (640, FIG. 6) is then closed, and the reactor 700 is then evacuated of quench gas with the vacuum pumping system. A NaK fill valve, connected to fitting 794, is then used to fill the reactor 700 with NaK as previously described. The gas transfer valve is then used to admit Argon, or some other suitable inert gas, to the reactor to push NaK back out of the reactor to the top of pipe 790. Both of these valves are then sealed closed and the pressure tight compartment re-established in preparation to deploy the instrument, such as into a well, borehole, or other space to be sampled for radiological constituents.

Rotary Valve

Figure 8:
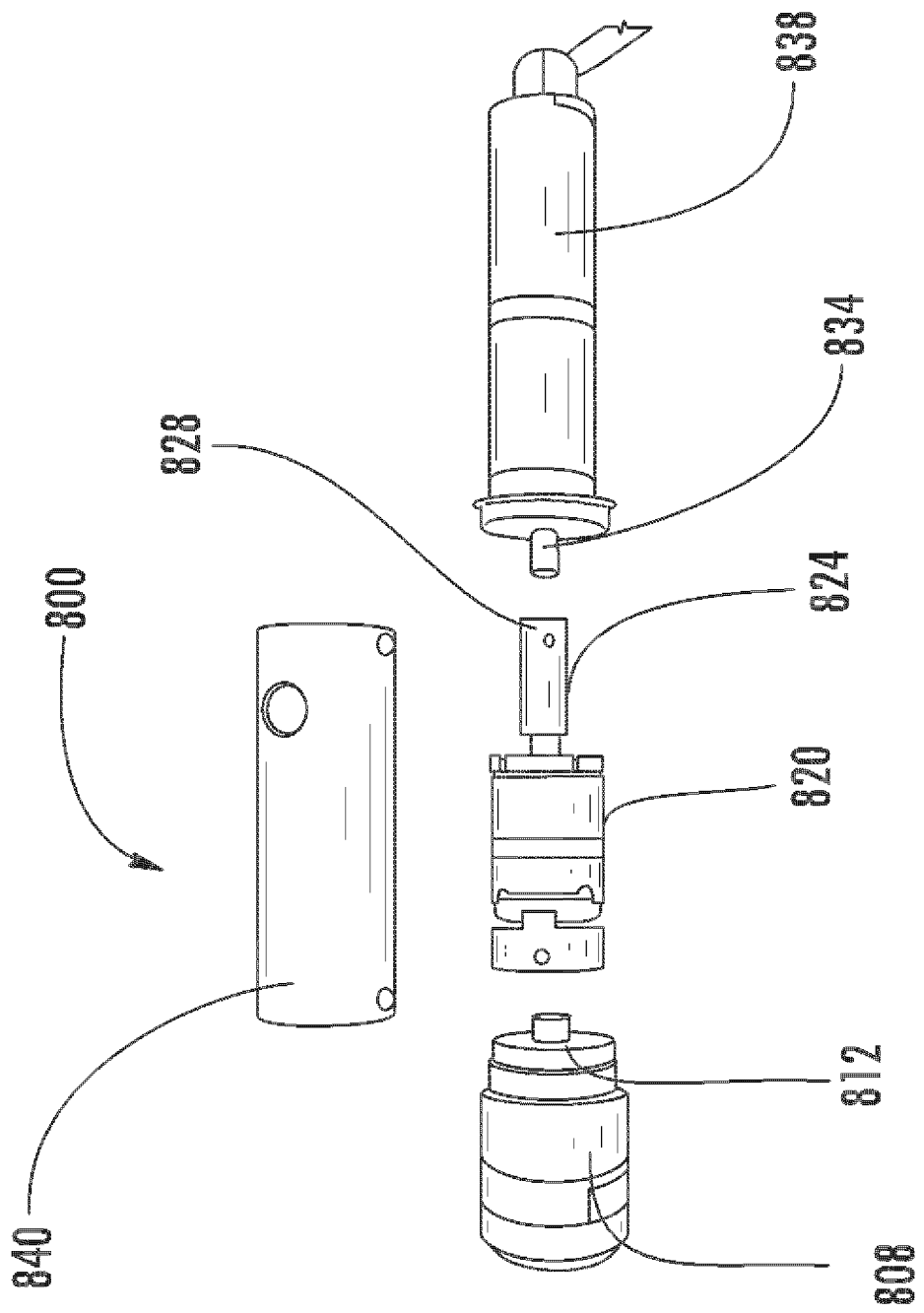
FIG. 8 illustrates a rotary valve for use with various disclosed embodiments, including in the radiation monitoring apparatus of FIG. 4.

In particular implementations, the sampling device 618, reactor 608, and detector 650 are selectively placed in communication through a rotary valve. Suitable rotary valves may be fabricated using a high performance liquid chromatography switching valve and a high performance motor and gearhead coupled through an adjustable slip clutch. FIG. 8 illustrates an example of a suitable rotary valve. The rotary valve 800 is constructed from a Rheodyne Corporation (Rohnert Park, Calif.) model 7000L HPLC valve 808 having an axially extending shaft 812. The axially extending shaft 812 is received by a mating aperture formed in an adjustable slip clutch 820, model SC-15 from Reell Corporation (St. Paul, Minn.). The adjustable slip clutch 820 has an axially extending transfer shaft 824. An aperture 828 is formed in the end of the transfer shaft 824 and is received by a mating drive shaft 834 axially extending from a motor 838, which in particular examples is a DC motor and planetary gear reduction case from Maxon Motors Corporation (Fall River, Mass.), models RE-25 and GP-26-B. The adjustable slip clutch 820 and the shafts 812, 824, and 834, are enclosed within a torque housing 840.

The rotary valve 800 switches flow from a sample source, such as a borehole or a condensation unit, to the sampling device 618, between the sampling device 618 and the reactor 608, and between the reactor 608 and the isolation valve 640. The rotary valve 800 may be used to interconnect additional components, such as chemical detectors, included in the device 600.

Detector

Gas scintillator detectors typically operate in a similar manner to liquid scintillation detectors in that a gaseous scintillant mixture reacts with radiation to produce light which is then quantified with a sensitive light detector. Compared to proportional detectors, scintillation-based tritium detector systems are potentially not as sensitive as gas-proportional detector systems. The chemical reactor retains most radioactive constituents contained in the water sample, producing a sample gas with comparatively little interfering radiation. Because the proportional and scintillation systems are typically of similar complexity and require similar mechanical and electronic equipment, it may be advantageous to use gas-proportional detector systems in many applications, particularly because of their greater sensitivity to low radiation particles.

Proportional detectors operate by directly quantifying the interaction of a charged particle with the detector. When a tritium atom decays by emitting a β-particle, the particle travels until it strikes a gas molecule where it is adsorbed and forms an electron-ion pair. If the voltage is high enough, the electrons from this primary ionization are given enough energy to ionize additional gas molecules in a process called secondary ionization. This results in charge multiplication that is proportional to the number of β-particles emitted. Thus, the proportional detector acts as a detector and signal amplifier in one unit. In some circumstances the interaction of the emitted electron with a gas molecule does not occur with enough energy to produce a secondary electron, but produces what is called 'simple excitation' of gas molecules. These excited gas molecules decay to their ground state through the emission of a photon. These photons can lead to additional photon-gas reactions, which lead to a loss of detector proportionality and chaotic signal behavior. To suppress the effects of simple excitation, a polyatomic fill gas is used to adsorb the simple excitation decay photon flux. This fill gas is referred to as a 'quench gas.' Proportional detectors typically operate at an applied potential of 1,000-3,000 volts.

The signal from a proportional detector can be "conditioned" to eliminate the contributions from other radiation, such as from radon. This is because radon emits a 5,590 KeV α particle versus the 18.6 KeV β particle of tritium. The detector amplifier electronics can be designed to discriminate between different decay energy signatures, which in turn allows the proportional detector to quantify both tritium and radon at the same time. The proportional detector 650 can be operated to detect the β decay from tritium even in the presence of high energy alpha and gamma radiation from other radioactive isotopes, such as radioactive isotopes naturally present in rock surrounding a well casing and in well water.

Suitable proportional detectors 650 may be constructed in a manner similar to the conceptual design described in Knoll, Radiation Detection and Measurement, 3d Ed. (2000). In a specific implementation, the detector 650 includes two charged surfaces, energized by the controller 656 and a high voltage power supply supplying various voltages up to 5 kV. In certain examples the body of the detector 650, which serves as a gas-tight vessel, is the cathode. In some examples, the anode is constructed of fine wire which can be present as a single, centrally placed electrode or as multiple wires arrayed radially about the central axis of the detector 650 body. In a specific example, the proportional detector 650 contains several fine wire electrodes (such as wires having a diameter of about $2.54 \times 10^{-3}$ cm) electrically insulated from the detector body. The use of multiple fine wire electrodes can improve detector sensitivity.

FIG. 9 illustrates an example of a proportional detector 900 useable in the devices of the present disclosure, including the instrument 600 (FIG. 6). The detector 900 includes a hollow cylindrical sheath 904 having a first end 908 and a second end 910. A detector assembly 912 is insertable into the sheath 904.

The detector assembly 912 includes a generally cylindrical upper pass-through fitting 914, such as a co-axial fitting rated for 25 kV. In the implementation of FIG. 9, the fitting 914 has an axially extending, hollow cylindrical protrusion 916. An electrical connector (not shown) is disposed in the protrusion. The electrical connector allows detector signals to be transmitted to other system components for processing and can provide an electrical feed through to energize the detector. In particular examples, the electrical connector is a gas-tight, high-voltage feed through from CeramTec North American Corporation (Laurens, S.C.), Part No. 17213-01-W. Two locking pegs extend radially outwardly from the protrusion 916 and allow the detector 900 to be connected to other components of an instrument.

The fitting 914 includes a mounting aperture 920 into which a mounting screw, bolt, or other fastener, can be inserted, such as to secure the detector assembly 912 to the sheath 904. An o-ring 924 is included in a groove in the fitting 914, which can help provide a tight seal between the fitting 914 and the sheath 904.

The electrical connector extends through the fitting 914 and an interior end of the connector is in connected to a push-pin electrical connector 928, which is in turn received by a mating copper connector 934. The copper connector 934 is disposed within a support nut (not shown), which is also connected to a gas transmission and support tube 938 and a ceramic insulator 940 having apertures through which six wires 942, such as 0.001 diameter stainless steel wires extend. The wires 942 are soldered in series and then to the copper connector 934. The wires 942 extend along a portion of the length of the tube 938. Two supporting ceramic insulators 944 are disposed along the length of the tube 938. The insulators have apertures 946 through which the wires 942 pass. The insulators 944 help maintain the position of the wires 942 and to prevent shorting of the wires 942, such as by touching the sheath 904 during use. A plurality of holes (not shown) are drilled in the sides of the tube 938.

A ceramic plate 950, through which the tube 938 passes, is disposed towards the bottom of the detector assembly 912. The wires 942 pass through the ceramic plate 950 and are secured and soldered together on the exterior surface of the plate 950.

The detector assembly 912 includes a fitting 960, which is generally constructed in a manner similar to the fitting 914, including having an o-ring 966 and a fastener aperture 970. The interior surface of the fitting 960 includes an axially extending connector 968 that receives the rod 938. A connector 980 extends from the exterior surface of the fitting 960 and may be used to attach the detector 900 to a gas input line 984.

During operation, the detector assembly 912 is placed within the sheath 904 and the assembled detector 900 is secured by inserting fasteners through apertures 926, 962 in the sheath 904 and into respective apertures 920, 970 of the fittings 914, 960.

During operation, the detector 900 is charged with a quench gas through a gas input line 984. The gas passes through the tube 938 and out of holes cross-drilled in the tube 938. A sample gas is similarly introduced into the detector 900. Radiation from the sample gas contacts the wires 942 and the signals are transmitted to a controller through the electrical connector 918. After a particular measurement, the detector 900 can be opened to a getter unit for removal of the sample.

Figure 10:
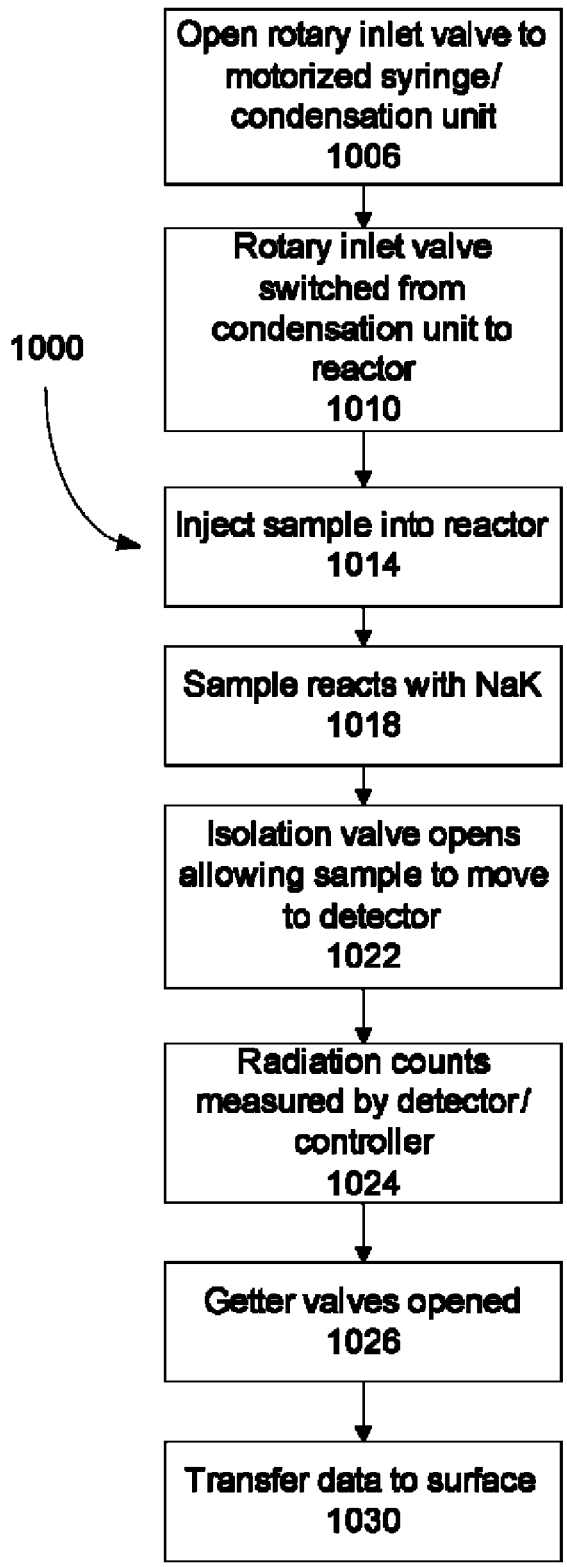
FIG. 10 is a flowchart of one disclosed embodiment of a method of operating a radiation monitoring apparatus according to FIG. 4, incorporating a rotary valve according to FIG. 8.

As discussed above, the operation of the device 600 is controlled by the controller 656 and proceeds according to a method 1000 illustrated in FIG. 10. At step 1006, the motorized high-pressure rotary inlet valve 800 of the instrument 600 is opened to the condensation unit 622 and the motorized syringe 618 pulses water into and out of the syringe barrel. This flushing removes water in the lines from the previous sample and assures that a representative sample goes to the reactor 608. At step 1010, the rotary valve 800 is closed to the condensation unit 622 and opened to the water decomposition reactor 608 after a final suction stroke of the motorized syringe 618. The motorized syringe 618, at step 1014, rapidly injects an aliquot of water into the reactor 608.

At step 1018, the aliquot of water reacts with a charge of 22 percent sodium-78 percent potassium alloy. The reaction produces hydrogen-tritium gas sufficient to generate a pressure of 75 psig (0.83 MPa) pressure in the reactor and solid sodium and potassium hydroxides. The hydroxide products have a larger specific gravity than NaK and sink to the bottom of the NaK pool, exposing fresh alloy for succeeding reactions and analyses until the NaK is depleted.

Following reaction of the sample and the NaK, at step 1022 the isolation valve 640 opens and allows the hydrogen-tritium gas to move into the proportional detector 650. The controller 656 operates the detector 650 and collects count statistics from the sample at step 1024. Once the count has proceeded such that a predetermined set of statistics are met, at step 1026 two additional solenoid valves 628, 632 open, allowing the hydrogen-tritium gas to enter the getters 626, 660. The getters 626, 660 contain a hydrogen sorbent 'getter' material that sorbs hydrogen onto a solid-phase substrate, removing hydrogen and tritium gas from the instrument. Following step 1026, the instrument 600 is ready for the next sampling event. At step 1030, data is transferred to a remotely located computer, such as a surface-located computer, from the controller 656. The surface computer may, in turn, send the data to a remote computer server, such as by land-line telephone, satellite phone, or radio frequency communications.

Figure 11:
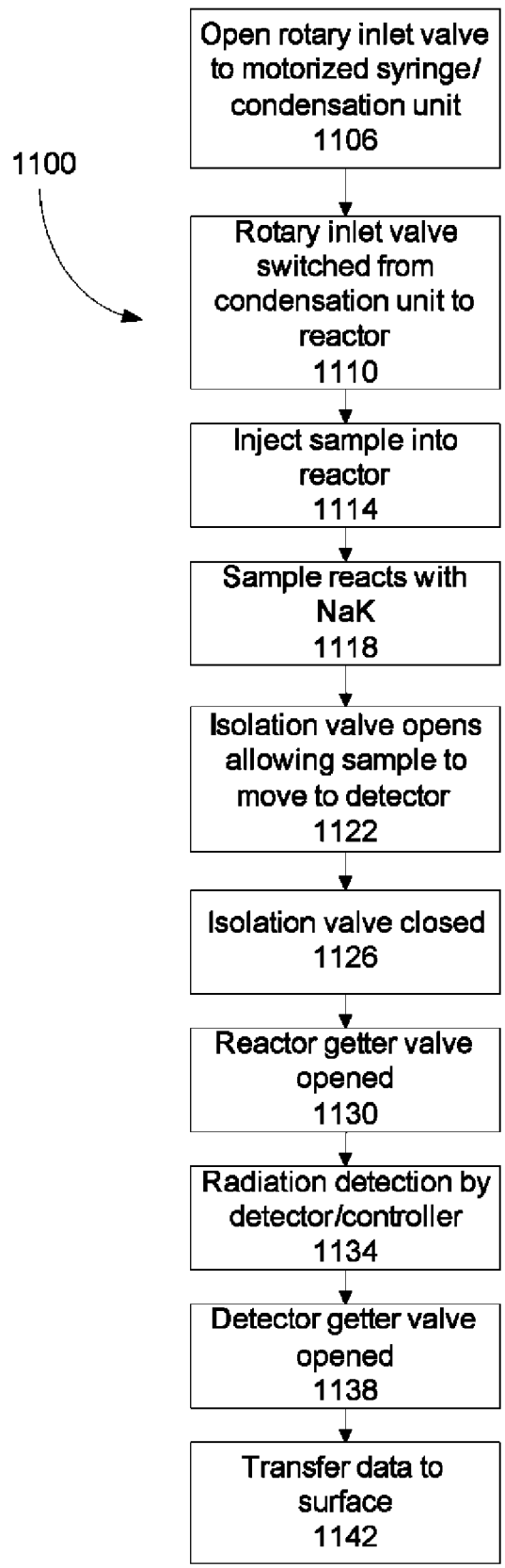
FIG. 11 is a flowchart of a method for operating a radiation monitoring apparatus, such as according to FIG. 4, incorporating a rotary valve, such as the valve of FIG. 8 and an isolation valve separating reactor and detector portions of the apparatus.

FIG. 11 illustrates an alternative method 1100 of operating the instruments 400, 600 having separate reactor and detector getter units. At step 1106, the rotary valve 800 connects the sampling device 618 to a sample source, such as the condensation unit 622. The rotary valve connects the sampling device to the reactor 608 at step 1110. The sample is injected into the reactor at step 1114. At step 1118, the sample reacts with the NaK, generating hydrogen and tritium gas.

The isolation valve 640 is opened at step 1122, allowing the sample gas to enter the detector 650. At step 1126, the isolation valve 640 is closed. Once the isolation valve 640 is closed, a reactor getter valve is opened at step 1130, allowing hydrogen to be removed from the reactor portion of the instrument 600.

At step 1134, tritium, or other radioactive material, is detected by the detector 650. Once detection has completed, a detector getter valve is opened at step 1138, allowing hydrogen to be removed from the detector portion of the instrument 600. At step 1142, data is sent from the controller 656 to a surface computer.

The disclosed monitoring instruments can be configured to fit within standard monitoring wells. Although particular disclosed exemplary computer packages are housed in a 10.16 cm diameter pressure housing, the computer boards can be designed to fit in others having different dimensions, such as a 4.45 cm diameter pressure housing. The 10.16 cm diameter instrument disclosed herein can be a standard design for most monitoring well applications. The instrument can be modified to meet the 4.45 cm diameter criterion for use in 5.08 cm diameter wells, such as by decreasing the size of the gas control valves.

The disclosed design may be modular and is adaptable to specific end-user requirements. The present disclosure provides, in certain embodiments, a monitoring device that provides:

Complete in situ operation: no material exchange between the borehole and the surface.
Solar powered with remote communication and complete computer control.
An outside instrument diameter of 1.75 in (4.45 cm), deployable down-hole in 2 inch (5.08 cm) diameter wells;
All stainless steel construction, deployable to pressures of 1,800 psig;
Lower detection limit of tritium in water of 1,000 picoCuries per liter (pCi/L);
Accuracy of ±3 percent at any activity up to 680,000 pCi/L (upper limit of laboratory testing).
Ability to interrogate a vertical zone of interest of about 12 in (30 cm);
Measurement capabilities for other physical properties, such as total conductivity, gross gamma, gross alpha, dissolved oxygen, pH, and temperature; and
Remote operation with solar and/or battery power.

It is to be understood that the foregoing is a detailed description of certain embodiments. The scope of the present disclosure is not to be limited thereby and is to be measured by the claims, which shall embrace appropriate equivalents.

EXAMPLE 1

Test of Proportional Detector and Active Metal Gas Generator

Figure 12:
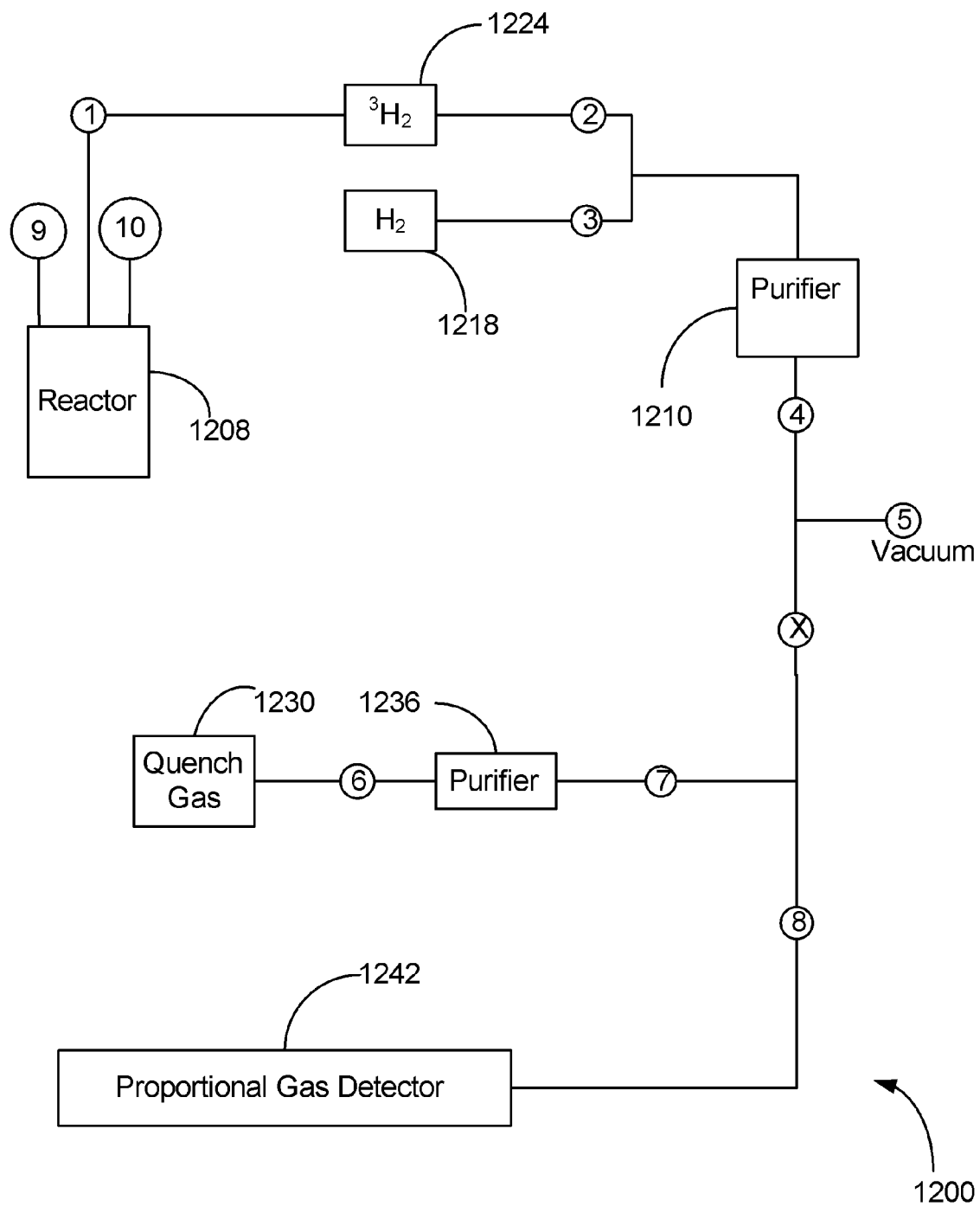
FIG. 12 is a schematic diagram of components of one disclosed embodiment of a test water decomposition reactor and proportional detector system.

A diagram of a plumbing system useable in a tritium monitoring device is shown in FIG. 12. The system 1200 is based on gasification of a water sample and proportional detection of tritium in the gas. The system 1200 contains a reactor 1208 for gasification of a tritiated water sample, a purifier 1210 to remove water from the gas, a hydrogen source 1218, at tritium source 1224, a $^{137}$Cs β source (not shown) for background calibration, a quench gas source 1230 and purifier 1236 used to maintain proportional conditions, and a proportional detector 1242 to analyze the hydrogen and hydrogen-tritium gas samples. In the initial tests conducted with the system illustrated in FIG. 12, a custom detector was fabricated by Ludlum Measurements, Inc.

Hydrogen-Tritium Gas Generation

Hydrogen-tritium gas was prepared as follows. One liter of water containing 1,000,000 pCi of tritium was placed in a pressure reactor and the gas space was evacuated. A stirrer was activated, and 25-g of sodium metal was simultaneously dropped into the water. Hydrogen-tritium gas representative of the 1,000,000 pCi/L tritium concentration of the water was instantly produced in the reactor. The generated gas was transferred to a gas storage cylinder to provide a uniform source of hydrogen-tritium for use in this Example 1.

Proportional Detector

The initial Ludlum detector used in this Example 1 was 91.44 cm long and had an outer diameter of 4.45 cm. The detector was constructed using 3.18 mm thick wall 316 stainless steel pipe and had a volume of 1.3 L. Up to thirty-six 0.025 mm diameter stainless steel wires were arranged equidistant from one another and parallel to a central 6.35 mm outer diameter 304 stainless steel tube that was located on the center axis of the detector tube. The central tube serves as the ground potential electrode while the stainless wires served as the positively charged electrodes. The potential across the electrodes was variable up to approximately 2.7 kV.

Several tests were conducted with the proportional detector to quantify detector response as a function of: quench gas composition and mixture ratio, operating pressure, and applied voltage. The operating characteristics were varied to optimize the detector response for linearity within the tritium activity range of interest: 1,000 to 1,000,000 pCi/L.

Pressure in the proportional detector system was measured with a transducer accurate to ±2 percent full scale. The entire gas handling system was leak tested with a helium leak detector. Tests were conducted by evacuating the system with a mechanical vacuum pump for at least 20 minutes. After leak testing, hydrogen gas was admitted to a predetermined pressure. The amount of hydrogen-tritium required for the test was then admitted. Finally, quench gas, usually propane, was admitted. Most tests were conducted at 1.3 atm (0.13 MPa) total gas pressure, but the range of pressures examined was from 1.0 to 3.0 atm (0.10 to 0.30 MPa). This procedure enabled testing of the tritium monitor over the tritium concentration range in water of 0 pCi/L to 700,000 pCi/L. One-minute duration counting tests were used to establish the basic shapes of the curves and the effects of variations in operating pressure or gas composition. Confirmatory tests lasted 10.0 minutes and the tests to develop the counts versus tritium concentration lasted 980.0 minutes.

Tests were originally conducted with the proportional detector positioned horizontally on the bench. Noticeable background variations were detected. Accordingly, subsequent tests were conducted with the proportional detector surrounded by 5.08 cm thick lead bricks. Surrounding the detector with lead bricks lowered the background detector response to a constant value.

As quench gas, early tests used 95% pure commercial propane passed through a 200 mL Oxyclear™ cylinder from LABCLEAR, Oakland Calif., to remove water and oxygen, as these constituents can interfere with the accuracy of the proportional detector. Later tests used 99.97 percent pure propane that was also passed through the Oxyclear™ cylinder. A similar gas purification procedure was followed for the hydrogen and the hydrogen-tritium. The 99.97 percent purity hydrogen and the hydrogen-tritium was passed through a different 200 mL Oxyclear™ cylinder before entering the proportional detector. These purification procedures generated consistent test results. The scatter observed in the counts may be due to the random uncertainty of the radioactive decay.

With reference to FIG. 12 (where valves are indicated by circled numbers), the operational procedure for operating the instrument for these tests was:

All of the lines were evacuated by opening valves 4, 5, 7 and 8.

Valves 5 and 7 were closed.

Valve 3 was opened to allow hydrogen for background readings to flow through the purifier and into the proportional detector until the pressure was 1.0 atmosphere.

Valves 3, 4 and 8 were closed.

Valve 5 was opened to evacuate hydrogen from the lines.

Valve 5 was closed and valves 6, 7 and 8 were opened to allow quench gas (propane or methane) to pass through a purifier and into the proportional detector until the desired concentration was reached (quench gas concentrations of 20, 30 and 40 percent quench gas were studied).

Valves 6, 7 and 8 were closed, and a background radiation standardization curve of counts versus applied voltage was generated. Then a $^{137}$Cs γ radiation source was placed on the surface of the detector midway from the ends. A curve for background plus the $^{137}$Cs source was generated.

The proportional detector was evacuated by opening valves 5 and 8.

Figure 13:
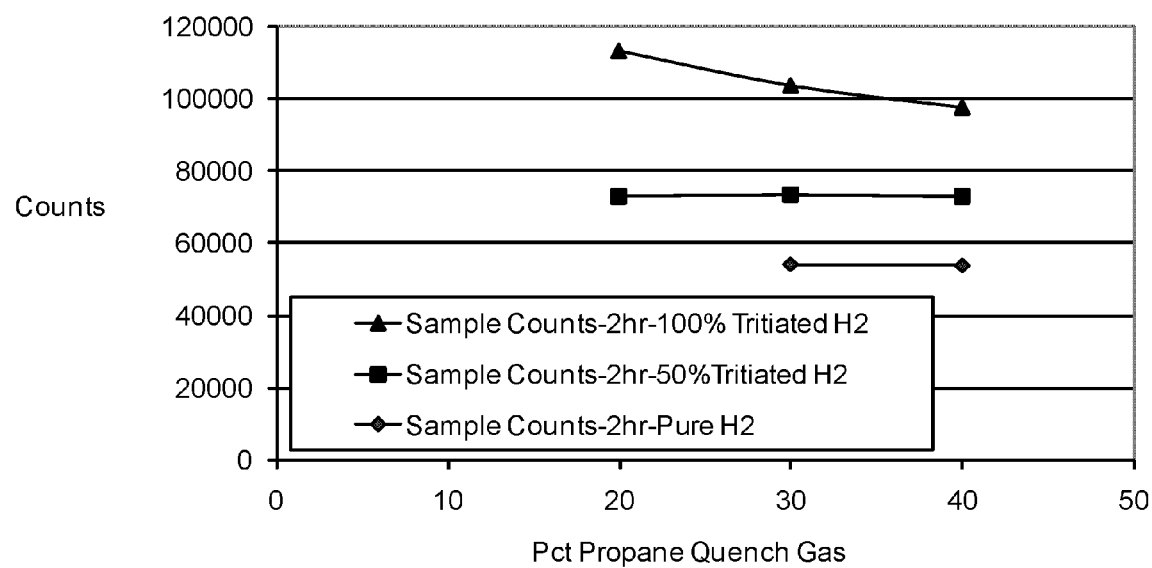
FIG. 13 is a graph of sample counts for samples having varying percentages of propane quench gas, illustrating proportional detector performance as the percentage of propane quench gas is varied for three different tritium activities: 0 (Pure $H_2$ gas), 500,000 pCi/L (50 percent tritiated $H_2$ gas), and 1,000,000 (100 percent tritiated $H_2$ gas) pCi/L tritium in water.

For developing the detector calibration functions using hydrogen/tritium, the above procedure was repeated but the hydrogen-tritium gas was used instead of pure hydrogen. The Ludlum detector results for a count-time of two hours are shown in FIG. 13. For 30 percent propane, the background count was 55,000 and the sample-plus-background count was 105,000. The standard deviation, σ, for this level is σ=(105,000)$^{1/2}$=324 counts. Recording a count of the background level plus σ represents a 95 percent confidence level. Because subtracting 105,000 counts from the background represents 1,000,000 pCi/L, and the target detection limit is 1000 pCi/L, 1000 pCi/L yields (105,000−55,000)/1000=50 counts. Fifty counts is smaller than σ (324 counts), so the detector could discern about 6,500 pCi/L with 95 percent confidence.

These results were from early tests in which the detector was not shielded from background radiation, the test conditions were not optimized, and the counting time was relatively short. In actual use in a well, the background will likely be lower because of shielding by the earth. In addition, longer counting times can be used to lower the uncertainty in the background. These measures should enable detection of tritium at 1,000 pCi/L.

EXAMPLE 2

Bench Scale Instrument

Figure 14:
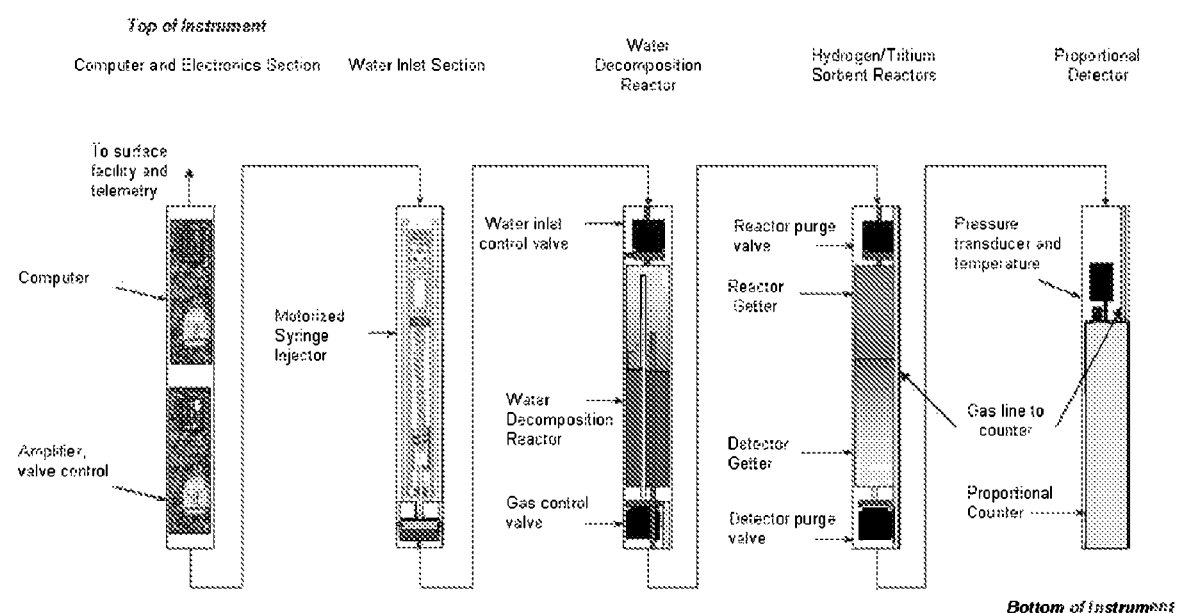
FIG. 14 is a schematic diagram of a bench-tested radiation monitoring apparatus.

A radiation monitoring device, shown schematically in FIG. 14, was designed and built. This instrument was configured to sample water in a groundwater well or unsaturated zone borehole, gasify the water sample, count the decay of gaseous tritium, and remove hydrogen-tritium gas through a hydrogen sorbent reaction.

The sample was introduced into the instrument through a hand operated valve and syringe apparatus. The syringe forced water into a reactive metal reactor where it was gasified into hydrogen-tritium gas. This gas was then directed into a proportional detector for tritium analysis. When the analysis was complete, as determined by count statistics collected by the on-board computer, the gas was removed from the system by a hydrogen-tritium sorbent reactor, or 'getter'.

The first instrument design included a sample collection-purging unit, a water decomposition reactor, a proportional detector, a hydrogen-tritium selective membrane and a hydrogen-tritium getter. However, the membrane was later replaced with a getter capable of sequestering the hydrogen-tritium gas in the presence of propane.

Water Decomposition Reactor

Initial tests were conducted in a Parr Instruments model 4561 autoclave. The diameter of the bomb portion was 6.35 cm i.d. with 6.35 mm thick walls. The bomb was 22.86 cm high. The head was equipped with six ports. The ports served the following purposes: admission of liquid NaK alloy, gas evacuation, water injection, pressure measurement, temperature measurement, and hydrogen-tritium gas outlet. Temperature measurement was made with a generic Omega chromel-alumel thermocouple. Pressure was measured with a generic Omega pressure gauge with a range of 0 to 300 psig (0 to 2.07 MPa).

NaK alloy was added to the reactor by pressurizing the supply cylinder with argon and using the argon to push the liquid alloy into the reactor through 3.18 mm stainless steel tubing. The 454 g NaK supply cylinder was located on a top loading balance. The mass of NaK admitted to the reactor was determined by the change in mass of the supply cylinder after passage of the NaK from the cylinder into the reactor. This weighing system was shown by preliminary tests to be accurate to ±1 gram. Water was injected into the reactor with a standard 3 mL hypodermic syringe with a 22-gauge needle. This injection method was found by gravimetric analysis to be accurate to ±0.1 mL.

The general operation of this reactor proceeded as follows. Air in the reactor was evacuated with a mechanical vacuum pump. After the air was removed, a valve in the NaK feed line was opened and NaK added until the supply cylinder had lost the number of grams required for the test. After the desired amount of NaK was added to the reactor, the NaK valve was closed. A valve between the hypodermic syringe and the reactor was opened and the plunger to the syringe was simultaneously pushed until the proper amount of water was injected. The NaK instantaneously reacted with the water sample. Constant pressure was exerted on the syringe plunger until the valve was closed.

Usually, sufficient NaK had been added to the reactor to conduct several tests, so the water injection procedure was repeated until the NaK was completely reacted. Upon exhaustion of the NaK, additional water was added to the reactor until all of the NaOH and KOH reaction products dissolved. The reactor head was then removed and the strong caustic solution poured out. The bomb and head were washed with water and dried before reassembling the reactor for the next test series.

Two additional reactors were constructed from stainless steel pipe fittings having diameters of 6.35 cm and 2.54 cm. These reactors demonstrated that a water sample could be reliably gasified and the gas drawn off for analysis.

Valves

Two types of valves were used in the instrument. Electrically operated solenoid valves were used for gas flow control. These valves were obtained commercially from Snap-Tite, Inc., and were either magnetically-latching or non-latching valves. Magnetically latching valves were used in locations requiring the valve to be opened for extended periods of time, whereas conventional non-latching types were used for quick acting applications. Magnetically latching valves were used on the getters, while a non-latching valve was used for the isolation valve.

Syringe

A motorized syringe made for the purpose of injecting tracer into a well was examined as a possible means to inject water into the reactor. Initial modifications were made to this syringe such that the stroke length could be readily changed, and the electronics were bypassed to allow direct communication between the controller and the syringe motor. Experiments were conducted with the syringe to evaluate the quality of the injectate stream during operation. The injectate stream must be of sufficient force to penetrate into the reactant pool in the reactor to promote a complete reaction.

Activated Carbon Sorption of Radon

Tests were conducted to determine the ability of activated carbon to remove radon from gaseous samples. A test apparatus was constructed which included a radon source, a hydrogen carrier gas source, an activated carbon sorption module, a hydrogen-radon collection container, and a scintillation counter. The radon source was a Pylon RN 150 unit, available from Pylon Electronics, Inc., of Mississauga, Ontario. A Ludlum Measurements, Inc. (Sweetwater, Tex.), Model 218 scintillation detector flask was used. A Ludlum Measurements Model 2200 scalar or a Ludlum Measurements Model 2000 scalar was used to record the counts. The scintillation chamber was a closed 8.89 cm by 10.16 cm high Plexiglas cylinder. Zinc sulfide scintillator paper lined the surface of the cylinder walls. The activated carbon module was a section of 0.95-cm o.d. stainless steel tubing. To vary the amount of carbon in the apparatus, the length of the carbon module was varied from 5.05 cm to 25.4 cm.

During each test, the system was evacuated with a mechanical vacuum pump for 30 minutes. After evacuation, radon was injected into the carrier gas. This gas mixture was metered into the evacuated gas collection system at a controlled rate. The gas passed through the activated carbon module and into the scintillation chamber. Gas flow was stopped when the pressure reached 1.0 atm (0.10 MPa) in the scintillation chamber. The activity of the gas in the scintillation chamber was measured immediately after its collection to detect the presence of daughter products that passed through the carbon. Counting time was 10 minutes. Counts were compared to counts for gas collected without the activated carbon module in place.

Hydrogen-Tritium Getter

Two types of getter materials were used. The first type was a metallic getter. The second type was a polymeric getter. The polymeric getter has platinum groups. Suitable polymeric getters are available from Sandia National Laboratories. One such class of materials is described in U.S. Pat. No. 7,001,535, incorporated by reference herein.

Propane or methane will typically poison metallic getters. However, it has been reported that polymeric getters remain effective in the presence of these gases. Metallic getters can typically be regenerated, while polymeric getters cannot typically be regenerated. Samples of each type of getter were obtained from Vacuum Energy Corporation and from SAES Getters USA, Inc. (Colorado Springs, Colo.), part number ST 198. The getters were placed in a test apparatus to determine their suitability for use in the radiation detection instrument.

The test apparatus for the hydrogen-propane getters used the proportional detector vessel as its gas source. The proportional detector was oriented either horizontally or vertically for these tests. Stainless steel tubing containing a pressure transducer passed from the detector up to a module containing the getter material. A second stainless steel tube returned purified quench gas to the proportional detector. Gas flow occurred due to the density difference between the hydrogen-propane feed (lighter) and the propane passed by the getter (denser). Hydrogen sorption, 'gettering', was monitored by the decrease in gas pressure. Tests were conducted at 1-3 atm (0.1-0.3-MPa) gas pressure. Variables studied during the tests included proportional detector orientation, piping size, propane concentration, and amount of getter. All tests were conducted at room temperature.

Assembled Test Radiation Monitoring Device

The components of the test version of the radiation monitoring instrument were machined, assembled and mounted onto a plywood panel. In certain embodiments of the test device, a motorized syringe is used in conjunction with the reactor solenoid valve to flush water from the lines and to inject a measured amount of water into the reactor. In certain tests, some of the components were mounted either on an adjacent lab bench or the floor to allow access to various instrument components. In further tests, rather than the computer controlled injector, a hand operated syringe was used to inject water into the reactor. The proportional detector was located within a cavity formed by lead bricks stacked such that a 10.16 cm square opening was maintained to the floor.

The reactor was machined from 0.32 cm wall, 316 stainless steel and was 78.74 cm long by 3.30 cm o.d. The head and the bottom screw into the tubing and were sealed with buna-n o-rings. In the reactor design used in this instrument, the hydrogen tritium gas passes through a riser tube and out the bottom of the reactor. The reactor was charged with NaK through the bottom. Water was injected through a 22-gauge (0.027-cm) needle that passed through the head and into the base of the reactor solenoid valve located immediately above the reactor. A generic Omega pressure gauge was plumbed into the gas line from the reactor to the detector to monitor the reactor pressure. Rather than the pressure gauge, pressure transducers may be used to monitor the pressure. A chromel-alumel thermocouple monitored the reactor temperature.

Gas from the water decomposition reactor passed through a cylindrical 10.16 cm long by 3.56 cm o.d. activated carbon module made by Swagelok Co. (Solon Ohio), model 304-HDF2-40 to remove radon. Swagelok tubing connectors were screwed into each end. The internal volume was 75 mL, and the module held approximately 40 g of 48C 12×30 activated coconut carbon obtained from Westates Vocarb Corporation (Siemens Water Technologies, Warrendale, Pa.). Even though radon was not used in these tests, the activated carbon module was included to study its effect on the hydrogen-tritium dynamics and the system hydrogen-tritium volume. From the activated carbon module, the sample gas passed into the proportional detector.

The proportional detector was a 91.44 cm long by 4.45 cm o.d. 316 stainless tube of 0.32 cm wall thickness. The bulkhead-style ends were sealed with o-rings and secured with screws that bear pull-out forces in shear. A high voltage feed through and a gas inlet-outlet passed through this bulkhead. A single $2.54 \times 10^{-3}$ cm diameter, 316 stainless steel wire was located along the axis of the tube and functioned as the high voltage wire. A pressure transducer monitored pressure in the detector.

The getter module was 105.4 cm long by 3.30 cm o.d. with 0.32 cm thick walls. The head and the bottom screw into the tubing and were sealed with buna-n o-rings. A 0.64 cm gas inlet tube of 304 stainless steel was connected to the top and bottom of the getter. Cartridge filters were placed at each end of the getter pipe. Polymeric getter material was placed in a nylon sock and loaded into the getter pipe after emplacing the bottom filter. The top filter was then emplaced and the top screwed on. The detector pressure transducer, obtained from Omega monitored pressure drop during gettering.

On-Board Electronics Package

The test device was controlled using a controller 656, as described with respect to FIG. 6 above.

Bench Scale Instrument Experimental Methods

A series of tests was conducted using the test device, as summarized in Table 1. Testing was conducted as follows. Each subsystem was checked out individually, then groups of systems were checked, and finally as the entire monitor unit was checked. The unit was then operated under the range of conditions expected in the field to obtain statistics to verify its ability to detect tritium. In general, testing proceeded as follows:

The 5.08 cm diameter pipe containing the detector was shielded with lead bricks. The lead bricks simulated the shielding provided by the earth.

The system was leak tested with a helium leak detector prior to operation.

Known tritium concentration hydrogen-tritium gas samples were placed in the bench detector and readings made.

Multiple analyses were made of a blank hydrogen sample to determine the precision of the detector.

Operation of the bench reactor was tested with a blank water sample.

Multiple decompositions were made of a blank water sample. Each gas sample was analyzed in the detector to determine the precision of the decomposition-detector combination.

Known tritium concentration water samples were injected into the reactor and the hydrogen-tritium gas was analyzed in the detector.

The proportional detector was operated for 16-hour count times with known concentrations of hydrogen-tritium gas over the concentration range 0 to 682,000 pCi/L to establish a standardized curve of counts versus tritium concentration. The statistical uncertainty of radioactive decay was determined from this curve. The lower limit of detection was the point where the increase in counts above background equaled the statistical uncertainty.

Water samples having known tritium concentrations were decomposed and analyzed. The results were plotted on the same page as the standard curve generated by analysis of gas of known hydrogen-tritium concentration. Accuracy was determined by taking the difference of the measured value for known tritium in water concentrations from the known tritium in hydrogen-tritium gas curve followed by dividing the obtained value by the known gas concentration value and multiplying by 100. This value should be less than ±10 percent of the standardized value.

The standard deviation of the set of five determinations made in the accuracy determination experiments was a measure of the sensitivity. A measurement within two standard deviations was taken as being within the 92 percent confidence limit; a measurement within one standard deviation was within the 95 percent confidence limit.

Test Device Results

Table 1 summarizes the types of test conducted, their purpose, and the number of each test conducted using the test device.

TABLE 1

Test and evaluation series that were completed with the TEST DEVICE

| Type of Test | Purpose | Number of tests |
|---|---|---|
| Physical Testing | Check for leaks & operational problems | 1 |
| Generate Standardization | Develop room temperature curve for tritium | 6 |

TABLE 1-continued

Test and evaluation series that were completed with the TEST DEVICE

| Type of Test | Purpose | Number of tests |
|---|---|---|
| Curve | concentration determinations | |
| Background Determinations | Determine room temperature background counts | 3 |
| Tritium Concentrations Determinations | Determine room temperature tritium concentration and accuracy over a range of concentrations | 3 |
| Precision Determinations | Determine statistical variation of background reading using blank sample | 8 |

Water Decomposition Reactor

One object of the water decomposition reactor tests was to determine if the NaOH and KOH reaction products would sink to the bottom of the liquid NaK alloy pool so that the succeeding water samples would contact fresh NaK alloy and completely react. Another object was to establish that there would be no reaction of the hydrogen-tritium with the NaK alloy. Once the operability of the reactor was confirmed, reactor conditions were optimized, such as by determining the amount of NaK alloy required per gram of water, heat of reaction effects, the best way to inject the sample, and how much unreacted NaK alloy remained in the reaction product layer.

Preliminary tests were conducted in the 6.35 cm Parr reactor because it had sufficient ports for all of the needs of the tests and was robust, in case unusual temperatures or pressures occurred in the testing.

Initial reactor tests employed only 6 g of NaK alloy to minimize potential problems. These tests established that the reaction of water with NaK alloy worked as predicted by the chemical equations. Reaction was virtually instantaneous and nearly complete. However, some unreacted NaK alloy remained in the hydroxide product layer.

To study a reactor suitably sized for a 5.08 cm diameter borehole, smaller reactors than the 6.35 cm Parr were used in subsequent tests. The initial test in the smaller diameter reactor used a 2.0 mL aliquot of water injected through a syringe into a 3.18 mm feed pipe that directed the water into the NaK alloy pool. The reactor contained 19 g of alloy. Pressure and temperature were monitored with a pressure transducer and a thermocouple. The hydrogen was evacuated from the reactor after each water injection. The reactor contents were allowed to cool before subsequent water injections. The test results are shown in Table 2.

TABLE 2

Hydrogen pressure and temperature per 2-mL water injection.

| Injection No. | Pressure Rise, psig (MPa) | Instantaneous Temperature Rise, ° C. |
|---|---|---|
| 1 | 18 (0.12) | 88 |
| 2 | 45 (0.31) | 380 |
| 3 | 37 (0.26) | 355 |
| 4 | 43 (0.30) | 416 |
| 5 | 23 (0.16) | 184 |
| 6 | 25 (0.17) | 255 |
| 7 | 0 | 0 |

The variation in the pressure and temperature rises indicated that the water was not completely reacting with the NaK alloy. The high temperatures noted were transient and quickly subsided to the range of 30-40° C. Further water injection tests indicated that when reaction was incomplete, water was retained within a hydroxide coating. The completeness of the reaction decreased when the water drop size was large and increased when the drop size was small. Hypodermic needles of various sizes were tested and it was found that a size of 22-gauge (0.027-cm) needle injector was small enough to consistently produce complete reaction.

Figure 15:
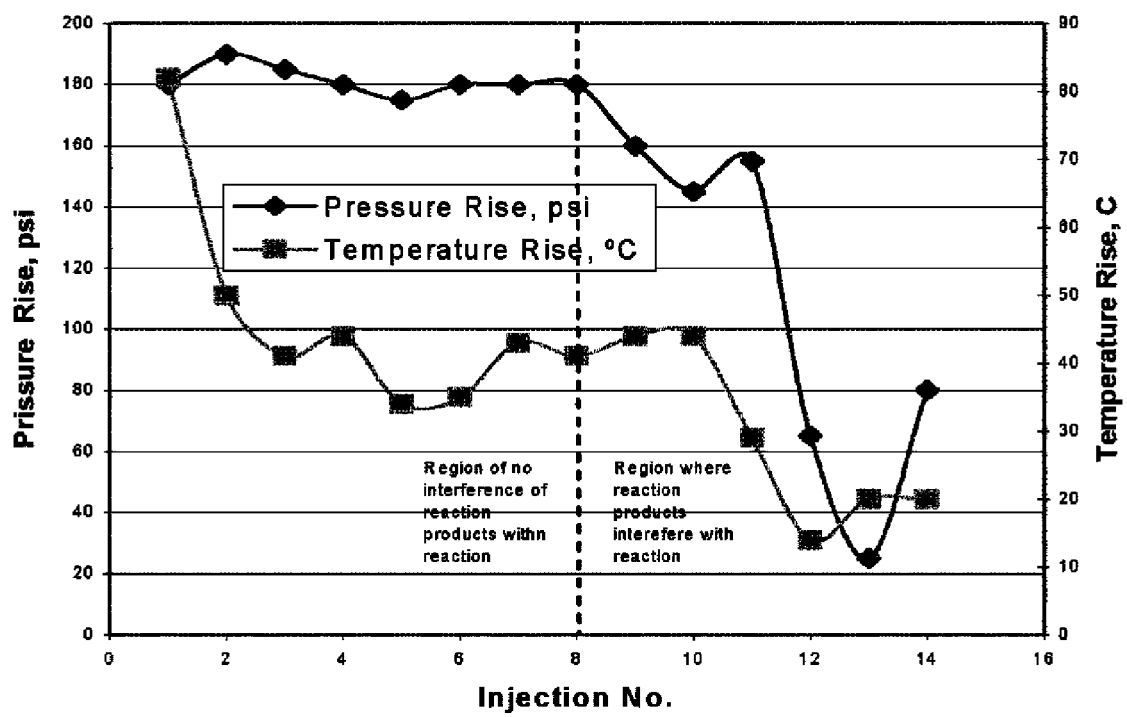
FIG. 15 is a graph of pressure rise (psi) versus injection number, illustrating hydrogen pressure and temperature rises per 1.7-mL water injection.

Results for a representative test using 37 g of NaK alloy with the 22-gauge (0.027-cm) needle are shown in FIG. 15. The pressures are much higher in FIG. 15 than in Table 2 because the gas-space of the reactor was reduced to investigate reactor operation at higher pressures. Also, the amount of water injected was reduced to the size aliquot needed to generate the proper amount of gas for the proportional detector. The temperatures were lower because the thermocouple was relocated to the outside of the reactor from the liquid alloy pool.

The results shown graphically in FIG. 15 demonstrate what happens inside the reactor with successive injections of water. Water aliquot usage and reaction consistency were excellent for the first 8 injections. Then a pattern of decreasing reaction was observed. Temperature decreases after injection 8. These data indicate that the hydroxide reaction products are interfering with the reaction after injection 8. In other words, there is no longer a pool of liquid alloy available for reaction with the water. The percent of alloy available for complete reaction with the water was calculated by adding the first 8 pressure aliquots, multiplying by 100 and dividing by the sum of all of the pressure aliquots. The sum of the pressures from the first 8 aliquots is 1450 psig (10.0-MPa); the sum of all of the aliquot pressures is 2080 psig (14.3-MPa). Percent available alloy=(1450×100)/2080=70 percent. This calculation indicates that complete reaction will occur as long as at least 70 percent of the alloy remains. Therefore, the reactor should carry 1.0/0.7=1.3 times the theoretical amount of alloy required for reaction to insure that complete reaction will occur with a given number of tests.

Another consideration in reactor design and operation is whether the depth of the NaK alloy pool negatively affects the usage factor and the completeness of reactions. A test using 115 g of alloy (22.86 cm pool depth) showed 80 percent NaK alloy use before complete water reaction was no longer observed. As a result of this test, and tests using smaller quantities of NaK alloy, a somewhat conservative usage factor of 70 percent was chosen for the design calculations.

The reactor was also studied to see whether reaction was occurring between the hydrogen-tritium product and NaK alloy. The reactor was charged with NaK alloy and then pressurized with hydrogen. The reactor was wrapped with heat tape and heated to 60° C., which is the temperature that is achieved due to the heat of reaction. Pressure was monitored over three hours. A drop in the pressure would indicate that a reaction was occurring between the hydrogen and the NaK alloy according to the reaction:

$$H_2 + NaK \rightarrow NaH + KH$$

No pressure drop was observed, indicating that there was no reaction between the hydrogen and the NaK alloy.

However, it was discovered that an unknown reaction occurs between the propane quench gas and the NaK. The proportional detector side of the instrument was isolated from the water decomposition reactor using an isolation valve. Two pressure transducers may be installed to monitor the pressure differential between the detector and the water decomposition reactor to allow computer control of the isolation valve.

Proportional Detector

The initial instrument experiments were conducted with the Ludlum detector. However, subsequent work employed custom designed and fabricated detectors. Two versions of a 1 L volume detector were designed and fabricated that met the diametrical specification necessary for a 4.45 cm overall diameter instrument package. These versions included a six-wire detector and a single-wire detector. Successive iterations on design and fabrication techniques led to increasingly higher performing detectors, and formed the basis for the field deployable 0.5 L detector design. One such device is shown in FIG. 9.

There was an effort to remove radon from the hydrogen-tritium gas stream prior to admission to the detector; radon is likely to be present in many testing conditions. A carbon-strip reactor was tested and found to be successful in removing radon. However, the addition of the carbon-strip reactor has the potential drawback of adding gas volume to the instrument, which in turn may indicate using a greater volume of hydrogen sorbent, additional NaK reserve, etc.

Because radon has a relatively short half-life of 3.8 days, it is possible to allow radon to naturally decay in the water decomposition reactor if the tritium activity sampling frequency is monthly, or quarterly. In addition, the proportional detector and associated amplifier and counter electronics are capable of discriminating between radon and tritium decay. These three methodologies are expected to adequately provide a method for removing or quantifying radon to permit an accurate quantification of tritium activity.

Figure 16:
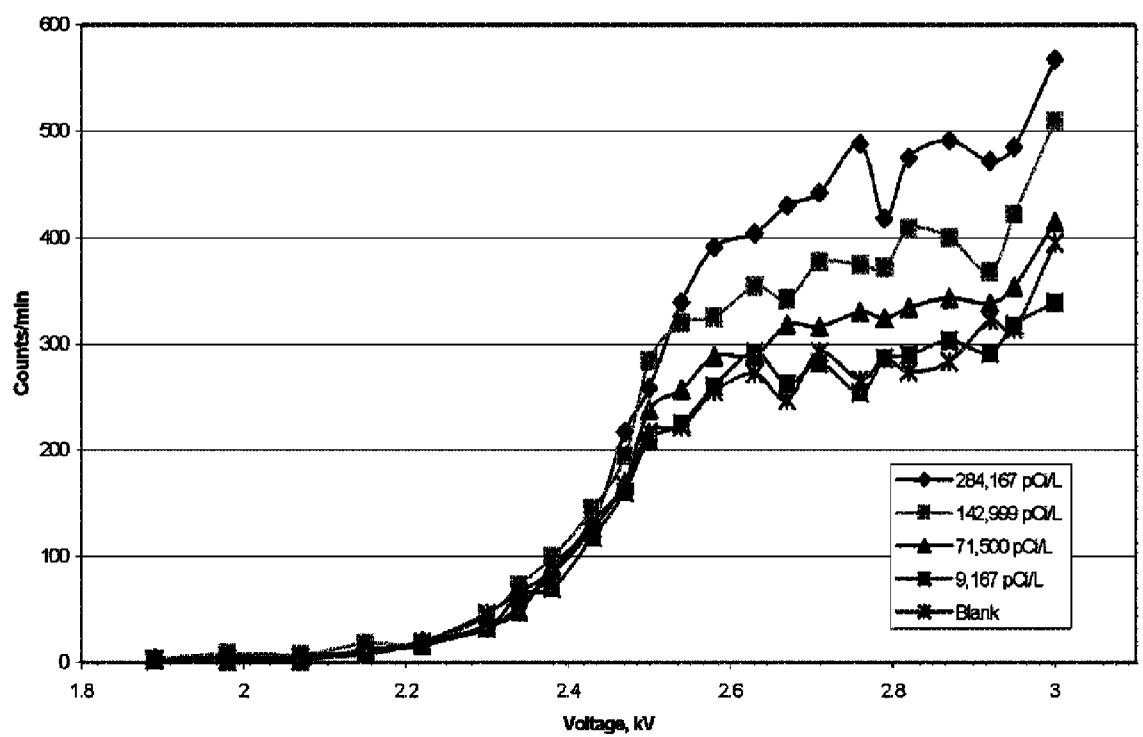
FIG. 16 is a graph of counts per minute versus voltage (kV), illustrating the effect of voltage on detector output for 1-minute counts at several tritium concentrations.

Tests were conducted to develop a plot of counts versus tritium concentration to 280,000 pCi/L with the lead shielded proportional detector. Several tritium concentrations, prepared by diluting 770,000 pCi/L hydrogen-tritium with hydrogen, as well as a blank composed entirely of hydrogen, were mixed with propane to a concentration of 67 percent hydrogen-tritium and 33 percent propane. When the sample was in the detector, the voltage was ramped from 1.89 kV to 3.00 kV in increments of about 0.05 kV. Each voltage was held for 2 minutes and the counts recorded. FIG. 16 illustrates plots of counts averaged to 1 minute versus voltage prepared from this data.

The resulting curves were all of the same basic shape, beginning from a low plateau from 1.9 kV to about 2.3 kV. The curve then rises steeply to about 2.5 to 2.6 kV. The curve then flattens out until about 2.9 kV at which point it rises steeply again. The first portion from 2.1 to 2.5 kV represents the proportional range and the region from about 2.6 to 2.9 kV represents the Geiger Müller (GM) range.

The response and calibration of the proportional detector at a fixed applied voltage was undertaken with tritiated water obtained from the Nevada Test Site 'E-tunnel' by reacting this water in either a commercial laboratory hydrogen generation system (Phase 1) and by generating hydrogen-tritium gas with this water using the test version of the instrument water decomposition reactor (Phase 2).

The Phase 1 test protocol for the proportional detector consisted of:
- Placing known tritium concentration hydrogen-tritium gas in the detector. The hydrogen-tritium gas was generated by reacting sodium metal with a Nevada Test Site E-Tunnel water sample in a commercial hydrogen generator. This sample contained 820,000 pCi/L of tritium at the time of sampling.
- Diluting the hydrogen-tritium gas with purified hydrogen gas to the concentration to be tested.
- Adding propane in the ratio of 1 volume propane to 2 volumes of the diluted hydrogen-tritium.
- All tests were conducted at 1.5 atm total pressure and room temperature.

Figure 17:
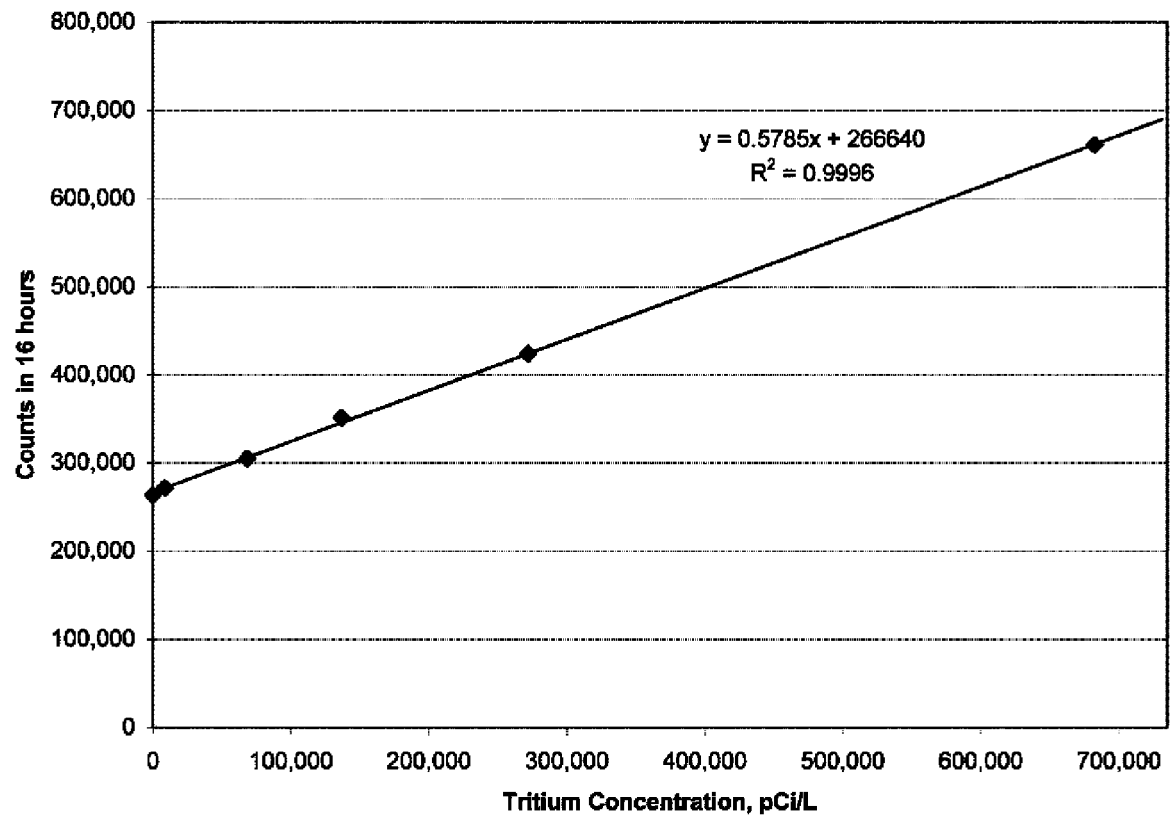
FIG. 17 is a graph of counts in 16-hours as a function of known tritium concentration in hydrogen-tritium gas at an applied voltage of 2.7 kV.

Counting at several tritium concentrations for 16 hours produced the following curve of counts versus tritium concentration, shown in FIG. 17. The curve is linear over the range of concentrations measured and has a slope of 0.5785 times the tritium concentration. At 1000 pCi/L, after 16 hours of counting, there would be 578.5 counts above background. This number of counts is greater than the statistical uncertainty in the background of 518.5 counts, indicating that the detector is sensitive to less than 1000 pCi/L tritium concentration.

Detector precision was also measured. Five determinations of the blank were made. Counting for each determination lasted 16 hours. The results are shown in Table 3.

TABLE 3

Detector tests using a blank hydrogen gas sample to determine background characteristics of the detector.

| Run No. | Counts in 16 Hrs |
| --- | --- |
| 1 | 259,233 |
| 2 | 259,613 |
| 3 | 258,550 |
| 4 | 258,241 |
| 5 | 258,799 |
| Sum | 1,294,436 |
| Average | 258,887 |
| Standard Deviation | 544 |

The standard deviation is a measure of the precision of the data. The standard deviation of 544 counts in 16 hours for the blank gas sample compares well with the statistical variation of 518.5 counts in the background radiation measurement of the detector. The slightly higher uncertainty in the precision of the blank was likely to due fluctuations in the system, including small variations in voltage, pressure, gas composition, temperature and capture of counts during the 16 hours of counting. These data show that the readings made by the proportional detector are still precise enough to discern 1000 pCi/L tritium concentration.

The Phase 2 test protocol for the proportional detector consisted of the following steps:
- An aliquot of Nevada Test Site E-tunnel water was diluted into several known lower tritium concentrations for injection into the bench water decomposition reactor.

Each water decomposition test was conducted with 2.5 mL of sample water. This amount of sample produced about 1500 mL (at standard temperature and pressure, STP) of hydrogen-tritium gas at 85 psig in the reactor. The hydrogen-tritium gas remained in the reactor to allow the pool of sodium-potassium alloy in the reactor to react with and remove any traces of moisture from the gas. These tests demonstrated that 30 minutes was sufficient for moisture removal.

After reaction, the hydrogen-tritium gas was rapidly metered into the detector. The detector was precharged with 333 mL (STP) of propane quench gas. The hydrogen-tritium and propane were allowed to mix for a sufficient time to allow for complete mixing, about 60 minutes.

Figure 18:
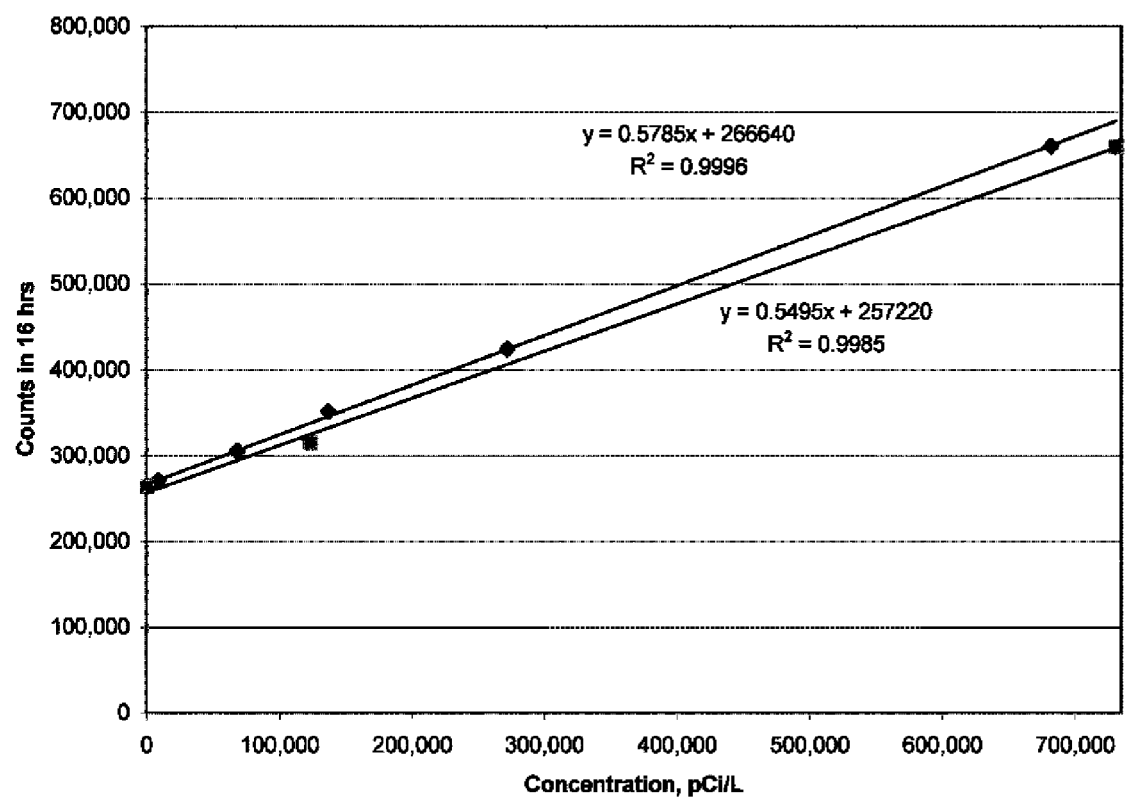
FIG. 18 is a graph of 16-hour counts for known tritium in gas and known tritium in water samples of various concentrations at an applied voltage of 2.7 kV. The diamonds represent hydrogen-tritium gas generated with a commercial hydrogen generator, and the squares represent hydrogen-tritium gas generated with a disclosed water decomposition reactor.

The voltage was set at 2.70 kV and tritium decay was counted for 16 hours. A curve of counts from three known tritium-in-water concentrations was plotted along with the curve produced from known tritium concentrations in hydrogen-tritium gas as shown in FIG. 18.

The two linear regressions exhibit similar slopes. However, the data generated with the test water decomposition reactor has a slightly smaller y-intercept than the data generated with hydrogen-tritium gas made with the commercial reactor. The difference was about 5 percent. This difference may be attributed to a small amount of water from each decomposition reaction not reacting and remaining entrained in the NaK pool in the test reactor. This water appears to decompose during subsequent decomposition reactions.

The three water decomposition reactions that define the curve were made in the order of low to high tritium concentration. Consequently, the measured activity for each of these analyses would be expected to be slightly lower than expected and is demonstrated by the lower slope of the linear regression for the bench reactor data. When analyzing a sample lower in activity than the preceding sample (results not shown), the proportional detector produced an apparent activity that was slightly higher than expected as a result of 'carry-over' of a small volume of higher activity water.

A check of the precision of the results from the combined water decomposition-analysis train was made by decomposing three blank water samples. The counts were 264,798; 264,782; and 262,505 counts in 16 hours of counting respectively. These results are consistent with similar tests conducted using known hydrogen-tritium gas compositions.

Hydrogen Getter Reactor Tests

Two different types of hydrogen sorbent, or 'getter' material were tested for use in the tritium monitoring instrument. Both types of material are commercially available, and represent hydrogen sorbents that would be suitable for an in situ monitoring instrument application.

Polymeric Getter

Sandia National Laboratory has developed polymeric getters for hydrogen adsorption. Three different polymeric getter compositions were obtained and tested. The first getter composition tested had a capacity of 100 mL of hydrogen per g of getter. In initial tests the first getter composition removed hydrogen from the detector at an operationally acceptable rate. The getter loaded to the advertised capacity.

The second getter composition had a capacity of 150 mL/g and a much faster hydrogen sorption rate. This getter composition removed the hydrogen over twice as fast as the first getter composition, and had higher sorption capacity. However, following exposure to hydrogen this second getter formulation formed a 'cake' or cementious mass that made it difficult to remove from the reactor. The formation of a cementious mass during sorption may lead to lower gas permeability of the getter material, thereby increasing the time required to remove hydrogen from the instrument. The first getter composition also formed a cementious mass. The third getter composition had a sorption capacity of 160 mL $H_2$/g, adsorbed hydrogen at an acceptable rate, and the spent getter was easily removed from the container with no apparent cementious behavior. Because of this success, the third getter composition was used for all subsequent tests.

Getter tests with the hydrogen-propane mixture demonstrated that hydrogen could be selectively removed from the gas mixture and that propane had no adverse effects on the getter. Getter tests were also performed with a hydrogen-methane gas mixture. These tests demonstrated that separating hydrogen from methane required nearly twice as much time as separating hydrogen from propane. The greater density of propane may be responsible for the greater ease of separating hydrogen from propane compared to separating hydrogen from methane.

A getter container was designed that measured 101.6 cm long by 2.86 cm inside diameter. This getter container can house enough polymeric getter for 30 in situ tests, assuming that 1 L of hydrogen-tritium gas would be removed from the detector and 0.6 L of hydrogen-tritium gas would be removed from the reactor for each test. In this design, the getter container was located directly above the detector. A 0.64 cm o.d. tube extended from the top of the detector to the top of the getter container. The getter container was filled with 100 g of getter, and the gas inlet and outlet were tightly packed with 5.08 cm of filter material to prevent loss of polymeric getter from the container. A series of getter tests was completed with this getter, and the results are shown in Table 4. For these tests, 0.5 atm of propane was added to the detector and the getter container. For each test, 1 L of hydrogen was added to the detector, which brought the detector to a pressure of 1.5 atm.

In tests 4-7, the 0.64 cm o.d. gas transfer tubes were replaced with 0.32 cm o.d. tubes to determine the effect of delivery tube size on the hydrogen removal rate. The smaller diameter tubes increased the hydrogen removal time by about 3 hr. The 0.32 cm o.d. tubes are advantageous since space can be limited within the in situ radiation detector pressure housing.

Figure 19:
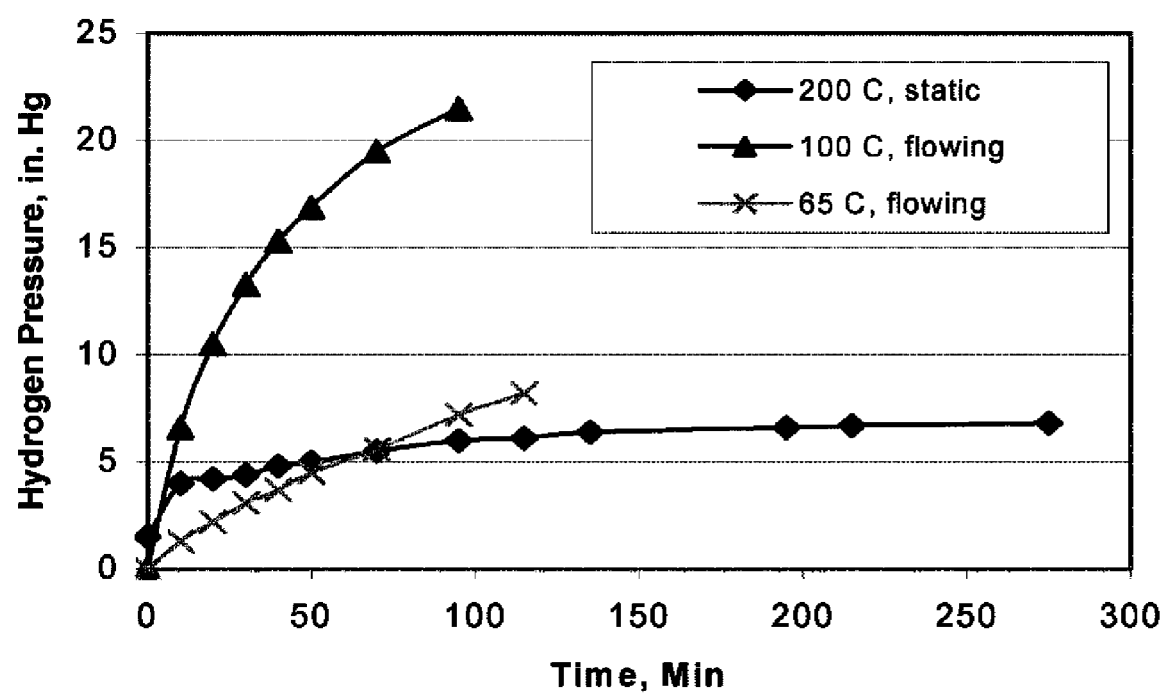
FIG. 19 is a graph of hydrogen pressure (inches of mercury) versus time (minutes), illustrating hydrogen removal versus time using a polymeric getter for consecutive loadings of hydrogen.

In tests 10 and 16 the normal gas flow direction was reversed for a short time. Under normal conditions, the valves between the detector and the getter were opened simultaneously. At the time the valves were opened, there was a large pressure differential between the detector and the getter chambers. As a result, gas rapidly flowed from the detector to the getter to equalize the pressure difference. In tests 10 and 16, only the valve on the return tube was opened during the gas surge. The concept of this operational change was to mechanically disturb the getter sorbent to try and prevent it from becoming consolidated to the point that gas flow would be subsequently restricted. In test 10, it appears from the data that there was an increase in the hydrogen removal rate as a result of this mechanical agitation. However, in test 16, no positive effect on gas flow rate through the bed was observed. The times at which 50 and 90 percent of the hydrogen was removed from the detector are shown in Table 4, and a plot of time versus temperature is shown in FIG. 19.

TABLE 4

Results of the polymeric getter tests.

| Time, | 1 | 2 | 3 | 4* | 5* | 6* | 7* | 8 | 9 | 10# | 11 | 12 | 13 | 14 | 15 | 16# | 17 |
|---|---|---|---|---|---|---|---|---|---|---|---|---|---|---|---|---|---|
| 50%, min | 20 | 15 | 10 | 20 | 25 | 15 | 20 | 30 | 45 | 20 | 40 | 55 | 60 | 75 | 120 | 190 | 24 hr |
| 90%, hr | 3 | 3.5 | 4 | 5.5 | 6 | 5.5 | 7 | 4 | 5.5 | 4.5 | 4.5 | 5.5 | 5.5 | 6 | 6.75 | 16 | |

*⅛ inch OD tubing for the feed line to the getter in these tests
Fluffed the bed The 90 percent hydrogen removal point was chosen as the point at which a new tritium detection test could begin in actual in situ tests. The data in the table show that through test 15, 90 percent of the hydrogen was removed in less than 7 hr.

Metallic Getters

Metallic getters generally have advantages over polymeric getters, including lower cost, higher hydrogen storage per unit volume, and reusability. However, organic gases such as propane typically poison metallic getters. For this reason, it was expected that a metallic getter would be used only to getter hydrogen from the reactor portion of the instrument. Since it is possible to employ separate getters for the reactor and the detector portions of the instrument, metallic getter compositions were evaluated.

The apparatus for these tests was similar to the apparatus used for the polymeric tests. A zirconium-nickel alloy was selected for these tests. The results of the tests demonstrated that the metallic getter removed essentially all the hydrogen from the reactor in a few hours. The rate of hydrogen removal with the metallic getter was somewhat slower than the rate measured with the polymeric getter, but the difference, which was on the order of 30 percent, is expected to be of no significance under normal operating conditions.

EXAMPLE 3

Field Instrument

The field deployable instrument was capable of sampling the borehole ten times before requiring extraction and servicing. A sample capacity of ten is suitable for an initial deployment where multiple sequential samples will be taken, and is also suitable for an extended deployment, sampling every five weeks or so for a period of one year. The instrument is scaleable to the needs of the end user as its sample capacity can be adjusted with relative ease.

The computer was placed at the top of the instrument to facilitate electrical connection with the geophysical wireline that serves as both the means to hang the instrument in the borehole, and to establish two-way communication with a surface-mounted computer and rf-communications equipment. The detector was placed immediately below the computer to minimize the length of coaxial wire required to connect the detector to the high voltage power supply. This design improvement allowed the use of a much larger diameter wire (lower noise, higher voltage rating) while eliminating the need to pass the high voltage wire between the detector and the high pressure instrument housing. Custom electronics packages were designed for the latching solenoid power supply, detector power supply, motorized syringe and high pressure valve power supplies, and detector signal conditioning. The on-board computer was an off-the-shelf Campbell Scientific Instruments (CSI) CR-1000 datalogger. Though the datalogger did not have the physical dimensional requirements to fit in a 4.45 cm o.d. package, it can be designed into a smaller diameter housing.

The detector was constructed as shown in FIG. 9. The detector was fabricated out of 316 stainless steel tubing and billet, high density machineable ceramic for electrical insulators, and $2.54 \times 10^{-3}$ cm diameter high tensile stainless wire for electrode material. An off-the-shelf 10 kV rated high pressure electrical coaxial feed through was used to connect the detector to the custom designed and fabricated power supply and signal conditioning components of the onboard computer system.

The instrument was based on a detector gas volume of 0.5 L as compared to the 1.0 L Ludlum detector. Because the instrument was designed to be deployed in an NTS well with a tritium activity approaching 200,000 pCi/L, the sensitivity of the 1.0 L laboratory detector design is not necessary, and a 0.5 L detector design reduced the overall length of the instrument. The length savings is a direct result of the scalability of the instrument since the water decomposition reactor and hydrogen getters are scaled to the volume of the detector. The detector was constructed with several electrodes arranged in a radial arrangement. The 0.5 L gas volume detector was expected to perform with a detection limit of 2,000 pCi/L and a sensitivity of ±5 percent at this activity level.

The getter reactor was split into two separate vessels, as it may be beneficial to isolate the metal alloy from the detector quench gas through an isolation valve. One getter was located immediately below the detector to adsorb hydrogen-tritium gas from the detector and associated plumbing down to the isolation valve. A separate reactor was located below the isolation valve and above the syringe injector to adsorb hydrogen-tritium gas from the reactor and associated plumbing up to the isolation valve. The hydrogen-tritium getter reactors were fabricated out of 316 stainless steel tubing and billet and incorporated magnetically latching electrical solenoid valves to control gas flow. The solenoid valves were operated by the on-board computer in conjunction with pressure transducers that allowed the computer to monitor gas pressure.

The water decomposition reactor was fabricated according to the design of FIG. 7 out of stainless steel tubing and billet, and incorporated a double buna-n o-ring seal design with a mechanical lock system that has a calculated burst pressure in excess of 1,700 psig with an expected peak reaction pressure of 75 psig.

The high pressure valve mechanism of FIG. 8 was used, as it can withstand a pressure specification of 1,800 psig and an instrument diameter specification of 1.75 inches. Many solenoid valves are pressure rated for 125 psig or less. A rotary valve was designed and fabricated using a high performance liquid chromatography switching valve and a high performance motor and gearhead coupled through an adjustable slip clutch, as shown in FIG. 8 and previously described.

The rotary valve switches flow from the borehole to the mechanical syringe and between the mechanical syringe and the water decomposition reactor. The mechanical syringe uses a motor-gearhead combination that is similar to that of the rotary valve. The mechanical syringe was modified to include an adjustable stroke, and was controlled with two limit switches used in conjunction with the on-board computer to inject borehole water into the water decomposition reactor. The adjustable stroke modification allowed for 'tuning' the volume of water injected into the water decomposition reactor to achieve a desired hydrogen-tritium gas pressure.

It is to be understood that the above discussion provides a detailed description of various embodiments. The above descriptions will enable those skilled in the art to make many departures from the particular examples described above to provide apparatuses constructed in accordance with the present disclosure. The embodiments are illustrative, and not intended to limit the scope of the present disclosure. The scope of the present disclosure is rather to be determined by the scope of the claims as issued and equivalents thereto.

I claim:

1. A sample collection method, comprising:
    condensing a vapor sample on a condensation surface of a cooling unit to form a condensate;
    collecting the condensate;
    decomposing the condensate;
    transferring decomposed condensate to a detector; and
    detecting for a component of interest in the decomposed condensate.

2. The sample collection method of claim 1, wherein the condensate is water.

3. The sample collection method of claim 1, wherein the condensate comprises tritiated water as a component.

4. The sample collection method of claim 1, wherein decomposing the condensate comprises reacting the condensate with at least one active metal.

5. The sample collection method of claim 1, wherein decomposing the condensate comprises electrolytically decomposing the condensate.

6. The sample collection method of claim 1, wherein the cooling unit comprises a Peltier cooler.

7. The sample collection method of claim 1, wherein detecting for a component of interest comprises using a proportional detector.

8. The sample collection method of claim 1, wherein the vapor sample is obtained from a well.

9. The sample collection method of claim 1, wherein the vapor sample is an ambient vapor sample obtained from a test site.

10. A monitoring device comprising:
    a condensation unit comprising a condensation surface, a cooler thermally coupled to the condensation surface; and a collection vessel in fluid communication with the condensation surface for receiving condensed fluid from the condensation surface;
    a detector in fluid communication with the collection vessel; and
    a decomposition reactor intermediate the collection vessel and the detector.

11. The monitoring device of claim 10, wherein the detector is a proportional detector.

12. The monitoring device of claim 10, wherein the decomposition reactor comprises an active metal.

13. The monitoring device of claim 10, wherein the decomposition reactor comprises an alloy of potassium and sodium.

14. The monitoring device of claim 10, the condensation unit further comprising:
    a housing at least partially enclosing the condensation unit; and
    an aperture formed in the housing for receiving a vapor sample.

15. The monitoring device of claim 14, the condensation unit further comprising a fan configured to draw air through the aperture.

16. The monitoring device of claim 10, wherein the cooler comprises a Peltier cooler.

17. The monitoring device of claim 10, wherein the detector is a proportional detector, the monitoring device further comprising:
    a quench gas source in fluid communication with the proportional detector; and
    a getter unit in fluid communication with the proportional detector.

18. The monitoring device of claim 10, wherein the detector is a proportional detector, further comprising:
    a quench gas source in fluid communication with the proportional detector; and
    a pump in fluid communication with the proportional detector, wherein the pump is configured to evacuate the proportional detector.

19. The monitoring device of claim 10, further comprising a transmitter, wherein the transmitter receives data from the detector and transmits the data to a computer.

20. A monitoring device comprising:
    a condensation unit comprising a condensation surface, a cooler thermally coupled to the condensation surface, and a collection vessel in fluid communication with the condensation surface for receiving condensed fluid from the condensation surface;
    a housing at least partially enclosing the condensation unit and having an aperture formed in the housing for receiving a vapor sample;
    a detector in fluid communication with the collection vessel; and
    a decomposition reactor intermediate the collection vessel and the detector.

21. A sample collection method, comprising:
    condensing a vapor sample on a condensation surface of a cooling unit to form a condensate;
    collecting the condensate;
    transferring the condensate to a detector; and
    detecting whether tritium is present in the condensate.

22. The method of claim 21, further comprising decomposing the condensate prior to detecting whether tritium is present in the condensate.

* * * * *